(12) United States Patent
Hulihan et al.

(10) Patent No.: US 12,115,169 B2
(45) Date of Patent: Oct. 15, 2024

(54) GANAXOLONE FOR USE IN TREATING TUBEROUS SCLEROSIS COMPLEX AND SEIZURE DISORDERS

(71) Applicant: Marinus Pharmaceuticals, Inc., Radnor, PA (US)

(72) Inventors: Joseph Hulihan, Radnor, PA (US); Alex Aimetti, Radnor, PA (US); Scott Braunstein, Radnor, PA (US)

(73) Assignee: Marinus Pharmaceuticals, Inc., Radnor, PA (US)

( * ) Notice: Subject to any disclaimer, the term of this patent is extended or adjusted under 35 U.S.C. 154(b) by 0 days.

(21) Appl. No.: 18/432,492

(22) Filed: Feb. 5, 2024

(65) Prior Publication Data

US 2024/0173336 A1 May 30, 2024

Related U.S. Application Data

(63) Continuation of application No. PCT/US2022/077419, filed on Sep. 30, 2022.

(60) Provisional application No. 63/252,106, filed on Oct. 4, 2021.

(51) Int. Cl.
*A61K 31/57* (2006.01)
*A61K 31/00* (2006.01)
*A61P 25/08* (2006.01)

(52) U.S. Cl.
CPC ............ *A61K 31/57* (2013.01); *A61K 31/658* (2023.05); *A61P 25/08* (2018.01)

(58) Field of Classification Search
CPC .................. A61K 31/57; A61K 31/658; A61P 25/08–12
See application file for complete search history.

(56) References Cited

U.S. PATENT DOCUMENTS

| | | | |
|---|---|---|---|
| 7,858,609 B2 | 12/2010 | Shaw et al. | |
| 8,022,054 B2 | 9/2011 | Shaw et al. | |
| 8,318,714 B2 | 11/2012 | Shaw et al. | |
| 8,367,651 B2 | 2/2013 | Shaw et al. | |
| 8,618,087 B2 | 12/2013 | Shaw et al. | |
| 9,029,355 B2 | 5/2015 | Shaw et al. | |
| 9,056,116 B2 | 6/2015 | Shaw et al. | |
| 10,603,308 B2 | 3/2020 | During | |
| 11,701,367 B2 | 7/2023 | Aimetti et al. | |
| 11,980,625 B2 | 5/2024 | Aimetti et al. | |
| 2019/0160078 A1* | 5/2019 | Masuoka | A61K 47/26 |
| 2021/0169824 A1* | 6/2021 | Guy | A61K 31/05 |
| 2022/0323424 A1 | 10/2022 | During | |
| 2023/0321117 A1 | 10/2023 | Aimetti et al. | |

FOREIGN PATENT DOCUMENTS

| | | |
|---|---|---|
| WO | 2007062266 A2 | 4/2009 |
| WO | 2019094724 A1 | 5/2019 |
| WO | 2020243349 A1 | 3/2020 |
| WO | 2021026124 A1 | 2/2021 |
| WO | 2021113834 A1 | 6/2021 |
| WO | 2022125408 A1 | 6/2022 |

OTHER PUBLICATIONS

"Pharmacokinetics & Pharmacodynamics: Dose Selection & the Time Course of Drug Action" by Holford et al. in Basic & Clinical Pharmacology, 7th Ed., edited by Katzung, Appleton & Lange (Stamford, Connecticut), pp. 34-49 (copyright 1998). (Year: 1998).*
Abstract and Corresponding Poster: "Ganaxolone Therapy Improves Interictal EEG and Seizure Control in Lennox Gastaut Syndrome in Patients with PCDH19 and CDKL5," Child Society for Neuroscience on Oct. 26, 2016.
Abstract and Corresponding Poster: "Ganaxolone Efficacy Observation in Patients with CDKL5 and PCDH19 with Lennox-Gastaut Syndrome Epileptic Encephalopathy: Seizure Reduction and EEG Findings," American Epilepsy Society, Abst. 1.180, Published Nov. 22, 2016.
ClinicalTrials.gov: "History of Changes for Study: NCT02358538, a Multicenter, Open-Label Proof-of-Concept Trial of Ganaxolone in Children with PCDH19 Female Pediatric Epilepsy and Other Rare Genetic Epilepsies," Publication Feb. 2015 and Jan. 16, 2017.
Press Release: "Marinus Announces Positive Preliminary Data for Children with CDKL5 Genetic Disorder," Published Jan. 23, 2017.
Press Release: "Marinus Announces Positive Preliminary Data for Ganaxolone," Published Jan. 25, 2017 (available at: https://www.drugdiscoverytrends.com/marinus-announces-positive-preliminary-data-for-ganaxolone/).
Marinus Pharmaceuticals Press Release "Marinus Pharmaceuticals Announces Key Business Updates for Tuberous Sclerosis Complex Program" May 17, 2024.
Singh et al., Intravenous Ganaxolone in Pediatric Super-Refractory Status Epilepticus: Two Case Presentations, The American Epilepsy Society Annual Meeting, Dec. 30, 2022, Retrieved from Internet<URL: https://marinuspharma.com/wp-content/uploads/2021/12/83027-GNX-in-SRSE-AES-Poster_2021-11-05_FINAL.pdf>, entire document.
Marinus Pharmaceuticals Press Release, "Marinus Announces Positive Preliminary Data From Children with CDKL5 Genetic Disorder", Jan. 23, 2017.
International Search Report for PCT/US2022/077419 dated Apr. 13, 2023.

* cited by examiner

*Primary Examiner* — Theodore R. Howell
(74) *Attorney, Agent, or Firm* — Hogan Lovells US LLP

(57) ABSTRACT

The disclosure to methods for treating tuberous sclerosis complex and epilepsy disorders comprising administering to a subject in need thereof a therapeutically effective amount of ganaxolone or a pharmaceutically acceptable salt thereof.

24 Claims, 11 Drawing Sheets

FIG. 10

| Somnolence-related AEs | | Age (yrs) | Weight (kg) | % change atonic sz | % change tonic sz | % change clonic sz | % change focal to bilateral tonic-clonic sz | % change generalized tonic-clonic sz | % change all focal sz | % change all major motor sz |
|---|---|---|---|---|---|---|---|---|---|---|
| NO | N | 28 | 28 | 3 | 17 | 2 | 5 | 14 | 10 | 27 |
| | Median | 4.5 | 16 | -100 | -37.9 | -100 | -60.1 | -35.25 | -45.6167 | -34.4 |
| Yes | N | 22 | 22 | 6 | 18 | 4 | 2 | 10 | 8 | 8 |
| | Median | 5.5 | 18.3 | -58.7 | -16.75 | -77.45 | -16 | -16 | -21.0156 | -17.75 |

| Dose (mg) | AUC$_{0-Last}$ (ng·h/mL) | C$_{max}$ (ng/mL) | C$_{min}$ (ng/mL) |
|---|---|---|---|
| 200 | 555 | 110 | 14.3 |
| 400 | 1030 | 169 | 39.4 |
| 600 | 1460 | 239 | 56.4 |
| 800 | 1450 | 263 | 52 |
| 1000 | 1510 | 262 | 56.9 |

GANAXOLONE FOR USE IN TREATING TUBEROUS SCLEROSIS COMPLEX AND SEIZURE DISORDERS

The present application is a continuation of International Patent Application No. PCT/US2022/077419, filed on Sep. 30, 2022, which designated the United States, which claims the benefit of U.S. Provisional Application No. 63/252,106 filed on Oct. 4, 2021, which are hereby incorporated by reference in their entirety.

1. BACKGROUND

Epilepsy is a chronic neurological disorder characterized by repeated seizures (>24 hours apart); by one seizure with a strong potential for recurrence (at least 60%). Chen et al., (2018), JAMA Neurol., 75(3):279-286. It affects people of all ages and results in social, behavioral, health, and economic consequences to the patients and their families. Id. It is estimated that more than 50 million people worldwide are affected. Id.

Antiepileptic drugs are the mainstay of treatment and suppress seizure occurrence without rectifying the underlying neuropathological process. Id. As a result, people with epilepsy often require life-long antiepileptic drug treatment. Additional therapeutic options include resective surgery, brain stimulation, and dietary therapy. In everyday practice, the choice of initial antiepileptic drugs on diagnosis currently depends mostly on syndromic classification, the treatment choice being framed by whether the epilepsy is deemed to be genetic generalized or focal in onset. Scheffer et al., (2017), Epilepsia, 58(4):512-21. This crude separation of the epilepsies depends on the clinical and electroencephalography features present at the time of diagnosis. Id. Moreover, despite new drugs for epilepsy, the rate of seizure freedom has remained largely unchanged across the decades.

EPIDIOLEX (cannabidiol (CBD)) was approved by the US FDA in 2018 for the treatment of seizures associated with Lennox-Gastaut syndrome (LGS) and Dravet Syndrome (DS), and in 2020 for the treatment of seizures associated with Tuberous Sclerosis Complex (TSC). See, FDA News Releases dated Jun. 25, 2018 Jul. 31, 2020 fda.gov/news-events/press-announcements/fda-approves-first-drug-comprised-active-ingredient-derived-marijuana-treat-rare-severe-forms; fda.gov/news-events/press-announcements/fda-approves-new-indication-drug-containing-active-ingredient-derived-cannabis-treat-seizures-rare. While FDA approval is limited to LGS, DS and TSC, there is growing use of CBD for treating medically refractory epilepsy that does not meet the diagnostic criteria of LD, DS or TSC. Abu-Sawwa et al. J. Pediatr Pharmacol Ther 2020 25 (6): 485-499. However, there is no evidence to support the use of CBD as monotherapy in patients with epileptic disorders, and there are concerns about drug and food interactions. Id. CBD has known drug interactions and effects on other drugs. It is recommended that when drugs that are substrates for UGT1A9, UGT2B7, CYP1A2, CYP2B6, CYP2C8, CYP2C9 or CYP2C19 are used in combination with CBD, that a reduction of the dose of such drugs be considered. See, EPIDIOLEX Prescribing Information, Revised September 2021. In particular, in vivo data show that EPIDIOLEX (CDB) increases plasma concentrations of drugs that that are substates of CYP2C19 when they are co-administered with EPIDIOLEX (CBD), and may increase the risk of adverse reactions to such drugs. Id. Coadministration of EPIDIOLEX (CDB) and clobazam (a CYP2C19 substrate) produces a 3-fold increase in the plasma concentration of N-desmethylclobazam, and active metabolite of clobazam, with no effect on clobazam levels, which may increase the risk of clobazam-related adverse reactions. Id.

Ganaxolone (3α-hydroxy-3β-methyl-5α-pregnan-20-one) is a synthetic neurosteroid and a positive allosteric modulator of the $GABA_A$ receptor. Ganaxolone interacts with both synaptic and extra-synaptic $GABA_A$ receptors and at binding sites distinct from benzodiazepines. Ganaxolone can act by regulating brain activity, which can include inhibiting abnormal electrical discharges that cause seizures and status epilepticus or restoring balance in disrupted neuronal activity in other central nervous system disorders. Ganaxolone is an approved drug for treating seizures associated with CDKL5 deficiency disorder (CDD), and under investigation for other diseases including TSC, refractory status epilepticus, established status epileptics and LGS.

Accordingly, there is a significant unmet need for safe and effective therapies for treating epilepsy disorders.

2. SUMMARY

This disclosure relates to methods for treating epilepsy disorders, such a TSC and/or TSC-related epilepsy.

As further described and exemplified herein, the inventors believed that ganaxolone could provide effective therapy for TSC and other epilepsy disorders. The inventors expected that administering ganaxolone three times daily with a total daily dose of no more than 1800 mg, as described in International Application No.: PCT/US2020/063648 would be effective in treating epilepsy disorders, such as TSC. However, it was unexpectedly discovered in a clinical trial of ganaxolone for treating seizures in TSC patients, that patients who were concomitantly treated with doses of CBD above 10 mg/kg showed lower suppression of seizure (efficacy) and experienced greater ganaxolone tolerability issues, in comparison to TSC patients who were not receiving concomitant CBD or CBD doses at or below 10 mg/kg. This result correlated with a higher blood concentration of ganaxolone (super therapeutic concentrations) in patients who were also receiving CBD in comparison to patients who were not receiving CBD.

Without wishing to be bound by any particular theory, the inventors believe that the results of the clinical study can be explained by a previously unknown and unexpected drug interaction between ganaxolone and CBD. This is unexpected because ganaxolone is metabolized by CYP3A4/5. Landmark et al. Epilepsia 2021 62:857-873. Ganaxolone is not significantly metabolized by the enzymes that are implicated in CBD interactions with other drugs: UGT1A9, UGT2B7, CYP1A2, CYP2B6, CYP2C8, CYP2C9 or CYP2C19.

Accordingly, it was unexpected that ganaxolone plasma concentrations, tolerability and efficacy would be affected by concomitant CBD. Subsequently, applicant conducted human pharmacokinetic studies of ganaxolone and CBD and those studies did not provide evidence of a pharmacokinetic drug-drug interaction. Thus, without wishing to be bound by any particular theory or mechanism, the unexpected drug-drug interaction could be a pharmacodynamic interaction.

As described further herein, the inventors also re-analyzed data from prior clinical studies to determine if ganaxolone-related tolerability issues, and particularly somnolence events (including somnolence, sedation, lethargy and fatigue) were associated with decreased efficacy. Unexpectedly, this analysis revealed that decreased efficacy of ganaxolone was associated with somnolence events. This was unexpected because the pharmacological activity of ganaxolone was known to induce somnolence events and it was understood that somnolence events would track with effective treatment. The inventors have now determined that administering of ganaxolone to treat epilepsy disorders, including seizures associated with TSC or CDD, using a ganaxolone titration that avoids, reduces or minimizes somnolence events can improve efficacy.

The inventors have now determined that the unexpected drug interaction between cannabidiol and ganaxolone can be mitigated or overcome by administering ganaxolone in a two phase titration. Similarly, undesired somnolence events can be mitigated or overcome by administering ganaxolone in the two phase titration. In the first phase, a lower starting daily dose of ganaxolone than has been used previously is administered for about a week, and then the daily dose is increased at lower increments that have been used in the past (typically each daily dose is administered for about 1 week) until the daily dose that correlates with the absorption limit determined from population pharmacokinetic modeling in pediatric patients is achieved. (See. FIGS. 7, 11A and 11B). Once that dose is achieved, the second phase of the titration commences, and the daily dose can be titrated to a target dose in larger increments. This titration schedule achieves a steady state plasma concentration of ganaxolone that is therapeutically effective (about 75 ng/ml to about 175 ng/ml plasma concentration) within about 4 to 5 weeks. If desired or indicated for additional seizure control, the dose of ganaxolone can be increased up to a maximum target dose of about 1,800 mg/day. An advantage of this two phase titration is that side effects are tolerized during the titration without a loss of efficacy. Accordingly, the two phase ganaxolone titration disclosed herein can be used to effectively treat seizure disorders, such as TSC, including in patients who are concomitantly receiving CBD, with improved tolerability. As such, the titration disclosed herein provides improved efficacy and safety, particularly in patient receiving concomitant CBD.

Another aspect of the ganaxolone titration disclosed herein, is that it can be used to reach a target dose of ganaxolone that is lower than the target dose that was used in prior clinical studies (i.e., lower that about 1800 mg/day or about 62 mg/kg/day). Typically, the titration achieves therapeutically effective plasma levels of ganaxolone (about 75 ng/ml to about 175 ng/ml) over about 4 to 5 weeks and the dose titration stops at about 1200 mg/day or about 42 mg/kg/day. If desired, the dose titration can continue to a target dose of about 1,800 mg/day. The titration to a lower target dose can improve tolerability of the therapy in all patients. This can improve efficacy, for example by reducing somnolence events and associated decrease in efficacy. This is particularly advantageous in patients receiving concomitant EPIDIOLEX (CBD), e.g. at a dose of more than about 10 mg/kg/day, and can avoid the super therapeutic plasma concentrations of ganaxolone that were associated with adverse events and reduced efficacy in the clinical study described herein in Example 1.

Accordingly, this disclosure relates to methods for treating epilepsy disorders, including TSC. The methods disclosed herein employ a two phase ganaxolone titration and are suitable for treating subjects who are not concomitantly being administered cannabidiol and subjects who are concomitantly being administered CBE at a low dose (e.g., about 10 mg/kg/day or less) or at a high dose (e.g., greater than about 10 mg/kg/day). In embodiments, the titration stops at a target dose of ganaxolone of about 1200 mg/day or about 42 mg/kg/day. In embodiments, the dose titration can continue to a target dose of about 1,800 mg/day. For example, a patient with seizure associated with an epilepsy disorder can be administered about 90 mg ganaxolone per day for about a week, followed by about 180 mg ganaxolone per day for about one week, followed by about 360 mg ganaxolone per day for about one week, followed by about 720 mg ganaxolone per day for about one week, followed by about 1,200 mg ganaxolone per day for the remainder of the treatment period. In embodiments, the patient is receiving concomitant EPIDIOLEX (CBD) at a dose of less than 10 mg/kg/day or preferably at a dose of 10 mg/kg/day or more.

In embodiments, this disclosure relates to a method for treating a seizure or epilepsy disorder, comprising administering to a subject in need thereof an effective amount of ganaxolone according to the regimen: a starting dose of about 90 mg/day to about 150 mg/day for about a week; then about 180 mg/day to about 300 mg/day for about a week; then about 360 mg/day to about 600 mg/day for about a week; then about 720 mg/day to about 1200 mg/day for about a week; and then continuing to administer ganaxolone at a dose of about 1200 mg/day up to about 1800 mg/day for the duration of the treatment period. The subject treated in accordance with the method can be receiving concomitant CBD treatment, such as low dose CBD treatment (e.g., an amount of 10 mg/kg per day or less) or high dose of CBD treatment (e.g., an amount of more than 10 mg/kg per day).

In embodiments, this disclosure relates to a method for treating a seizure or epilepsy disorder, comprising administering to a subject in need thereof an effective amount of ganaxolone according to the regimen: a starting dose of about 3 mg/kg/day to about 6 mg/kg/day for about a week; then about 6 mg/kg/day to about 12 mg/kg/day for about a week; then about 12 mg/kg/day to about 24 mg/kg/day for about a week; then about 24 mg/kg/day to about 42 mg/kg/day for about a week; and then continuing to administer ganaxolone at a dose of about 42 mg/kg/day up to about 63 mg/kg/day for the duration of the treatment period. The subject treated in accordance with the method can be receiving concomitant CBD treatment, such as low dose CBD treatment (e.g., an amount of 10 mg/kg per day or less) or high dose of CBD treatment (e.g., an amount of more than 10 mg/kg per day).

In embodiments, this disclosure relates to a method that comprises administering to a subject in need thereof ganaxolone in an amount of about 150 mg per day for about one week, followed by about 300 mg per day for about one week, followed by about 600 mg per day for about one week, followed by about 1,200 mg per day for about one week, followed by about 1,800 mg per day for the remaining treatment period. This method is preferably used to treat subjects 1) who are not concomitantly being administered cannabidiol, or 2) who are concomitantly being administered a low dose of cannabidiol (e.g., an amount of 10 mg/kg per day or less). This method can also be used to treat subjects who are concomitantly being administered a high dose of cannabidiol (e.g., an amount of more than 10 mg/kg per day).

In embodiments, this disclosure relates to a method that comprises administering to a subject in need 90 mg per day for about a week, followed by about 180 mg per day for about one week, followed by about 360 mg per day for about one week, followed by about 720 mg per day for about one week, followed by about 1,200 mg per day for at least about 1 week. The method can further comprise administering ganaxolone in an amount of up to about 1,800 mg per day following administration of ganaxolone in an amount of about 1,200 mg per day for about one week. This dosing regimen is preferably used to treat subjects who are concomitantly being administered a high dose of cannabidiol (e.g., an amount of more than 10 mg/kg per day). This dosing regimen can also be used to treat subjects 1) who are not concomitantly being administered cannabidiol, or 2) who are concomitantly being administered a low dose of cannabidiol (e.g., an amount of 10 mg/kg per day or less).

This disclosure also relates to a method that comprises administering to a subject in need thereof ganaxolone in an amount sufficient to achieve a ganaxolone plasma concentration of about 18 ng/ml to about 43 ng/ml for about 1 week, then in an amount sufficient to achieve a ganaxolone plasma concentration of about 37 ng/mL to about 87 ng/ml for about 1 week, then in an amount sufficient to achieve a ganaxolone plasma concentration of about 56 ng/ml to about 131 ng/ml for about a week, then an amount sufficient to achieve a ganaxolone plasma concentration of about 75 ng/ml to about 175 ng/ml for the remainder of the treatment period.

Any of the methods of this disclosure can be used to treat a subject with TSC. Any of the methods of this of this disclosure can be used to treat a subject with CDLK5 deficiency disorder.

3. BRIEF DESCRIPTION OF DRAWINGS

FIG. 1 is a graph depicting the proportion of subjects achieving≥50% reduction in TSC-associated seizure frequency in a clinical study of ganaxolone. The graph shows overall seizure reduction for all patients treated with ganaxolone (left column), patients treated with ganaxolone and concomitant cannabidiol (middle column), and patients treated with ganaxolone and concomitant everolimus (right column).

Figure 7:
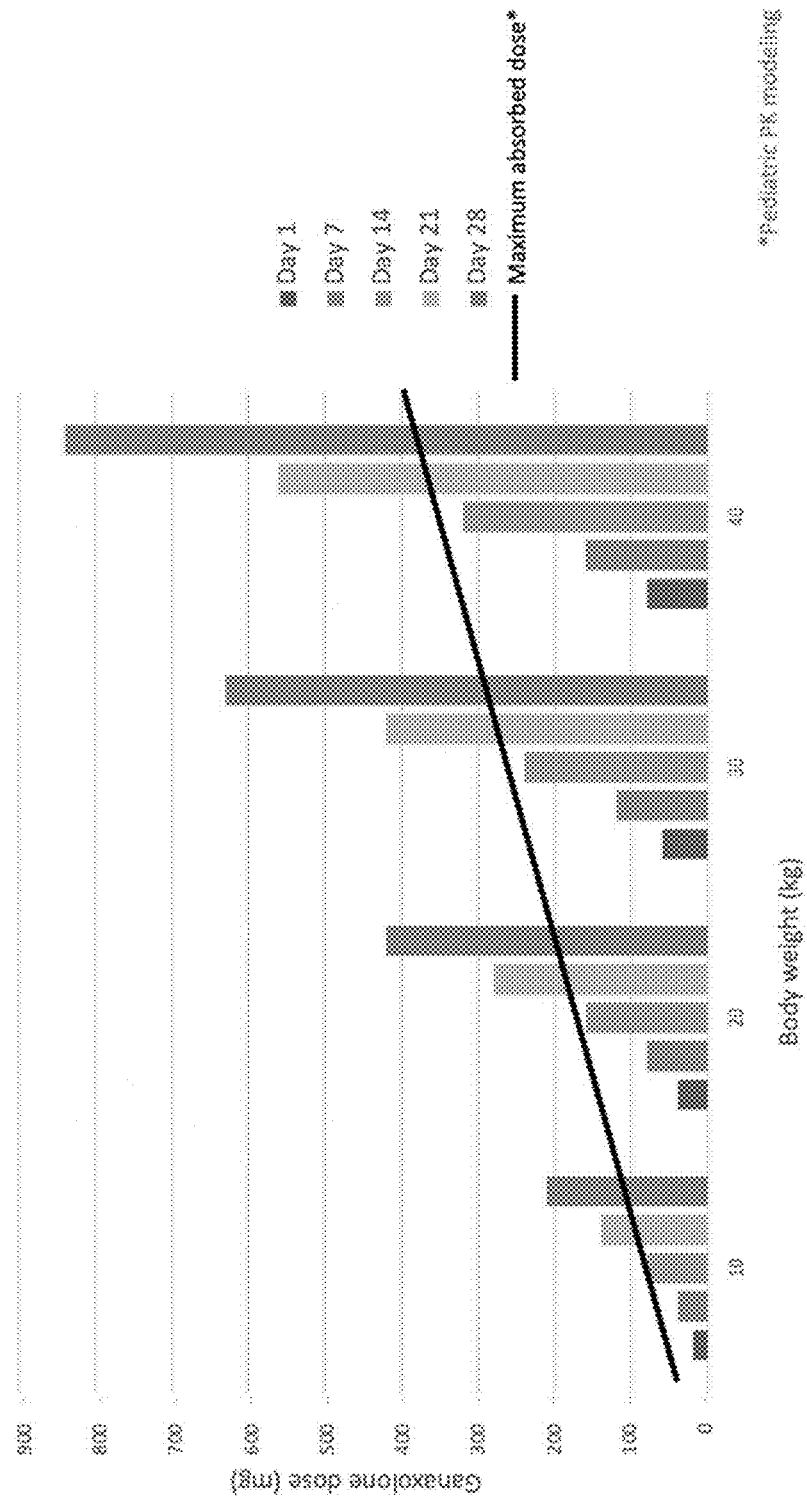

FIG. 7 is a graph depicting weekly titration amounts based on body weight. The titration starts at a lower initial dose of ganaxolone (lower than the initial dose that was administered in the study described in Example 1) with gradual increases until the absorption limit (maximal absorbed dose) as determined from population pharmacokinetic modeling in pediatric patients (diagonal line) is reached. The dose is lower and titration gradual until the limit is reached, after which the weekly dose increments are larger.

Figure 8:
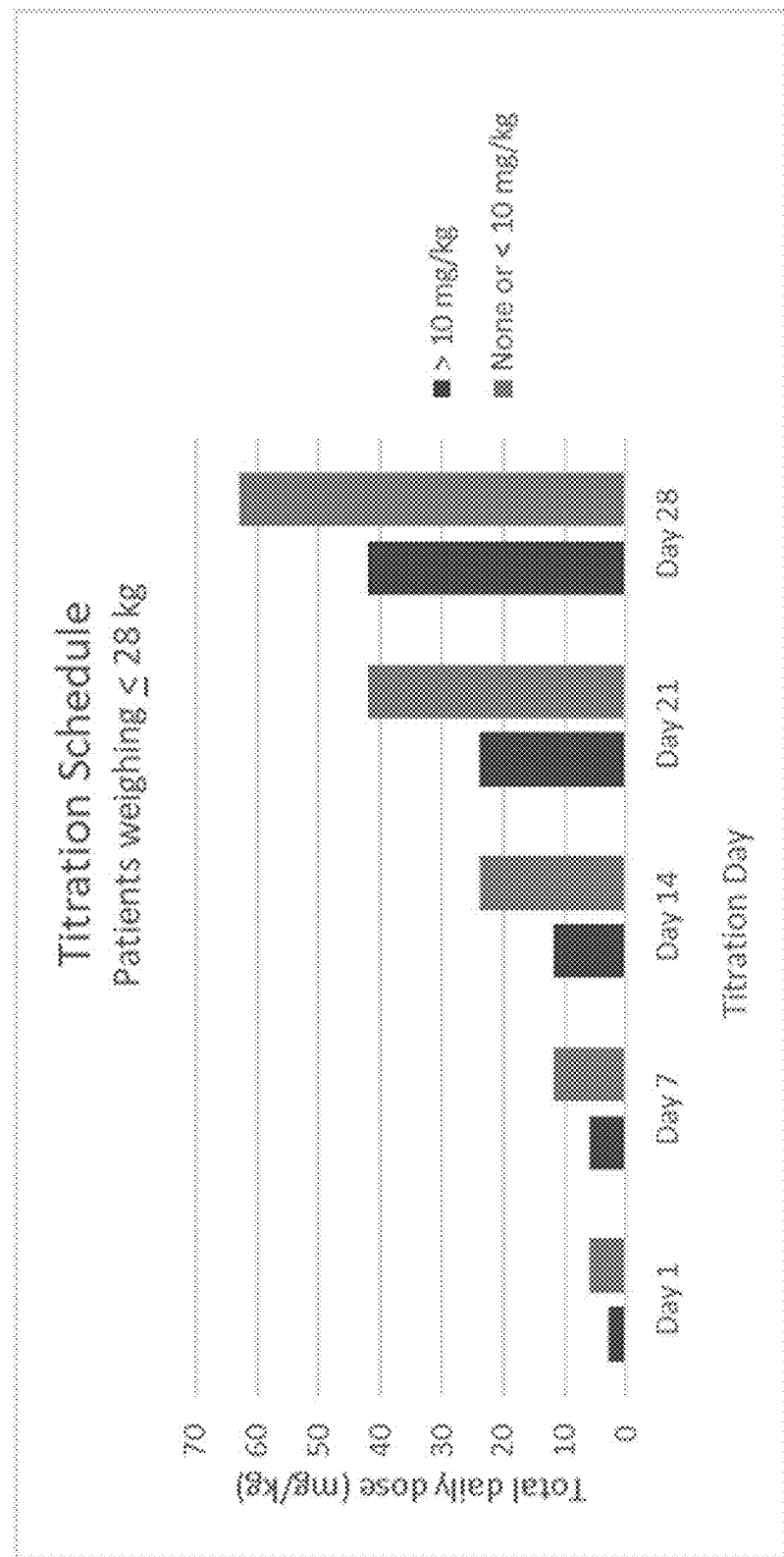

FIG. 8 is a graph depicting weekly titration amounts of ganaxolone based on body weight for patients weighing greater than 28 kg, and who are receiving concomitant EPIDIOLEX (CBD) at a dose greater than 10 mg/kg, or who are not receiving concomitant EPIDIOLEX (CBD) or concomitant EPIDIOLEX at a dose of less than 10 mg/kg. The ganaxolone titration for patients receiving concomitant EPIDIOLEX (CBD) at a dose greater than 10 mg/kg uses a lower starting dose, is more gradual and is capped at 42 mg/kg.

Figure 9:
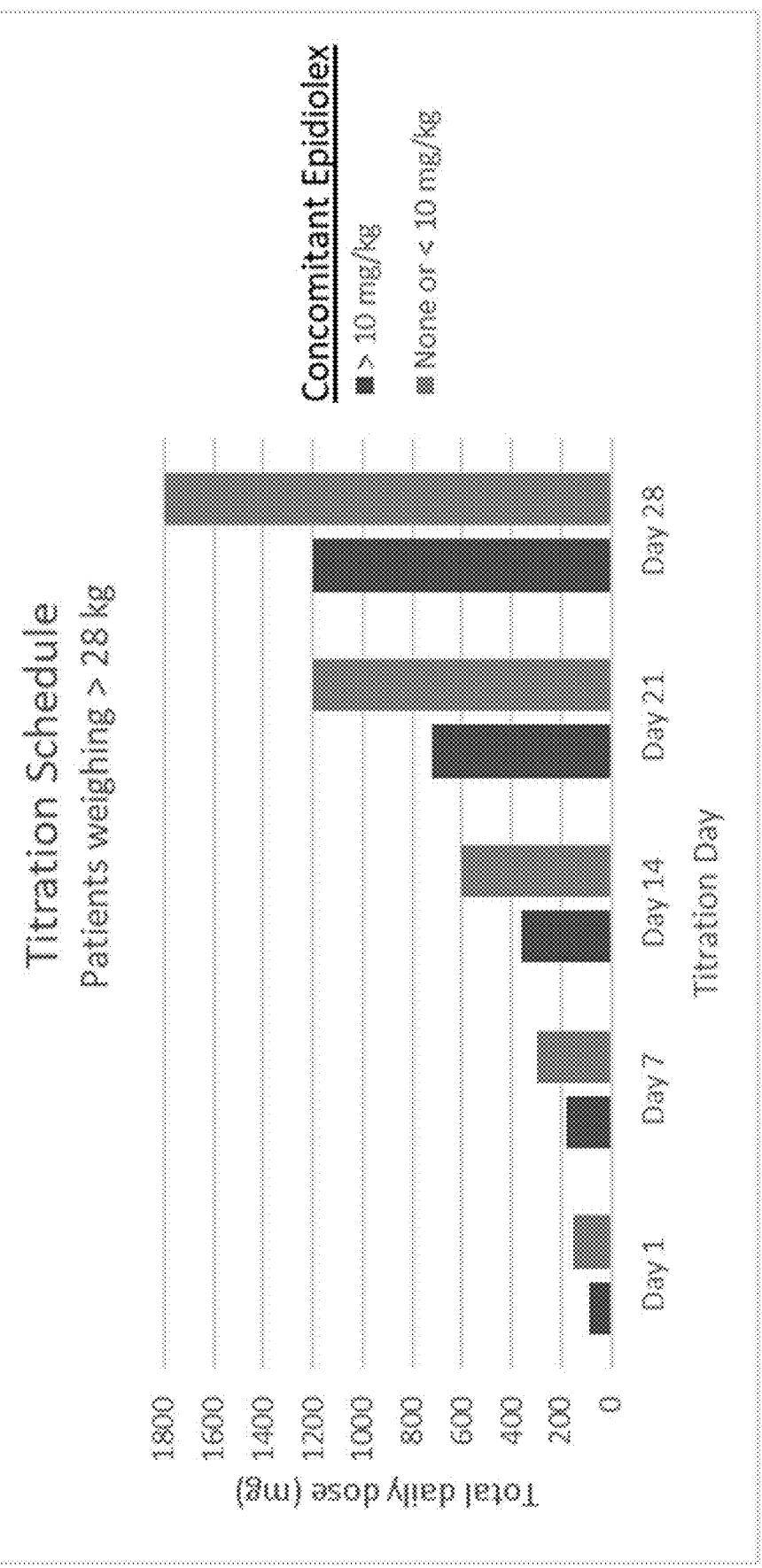

FIG. 9 is a graph depicting weekly titration amounts of ganaxolone based on body weight for patients weighing 28 kg or less, and who are receiving concomitant EPIDIOLEX (CBD) at a dose greater than 10 mg/kg, or who are not receiving concomitant EPIDIOLEX (CBD) or concomitant EPIDIOLEX at a dose of less than 10 mg/kg. The ganaxolone titration for patients receiving concomitant EPIDIOLEX (CBD) at a dose greater than 10 mg/kg uses a lower starting dose, is more gradual and is capped at 1200 mg/day.

FIG. 10 is a table presenting data from the ganaxolone treatment group of a phase 3 clinical trial of ganaxolone in CDLK5 deficiency disorder.

Figures 11A, 11B:
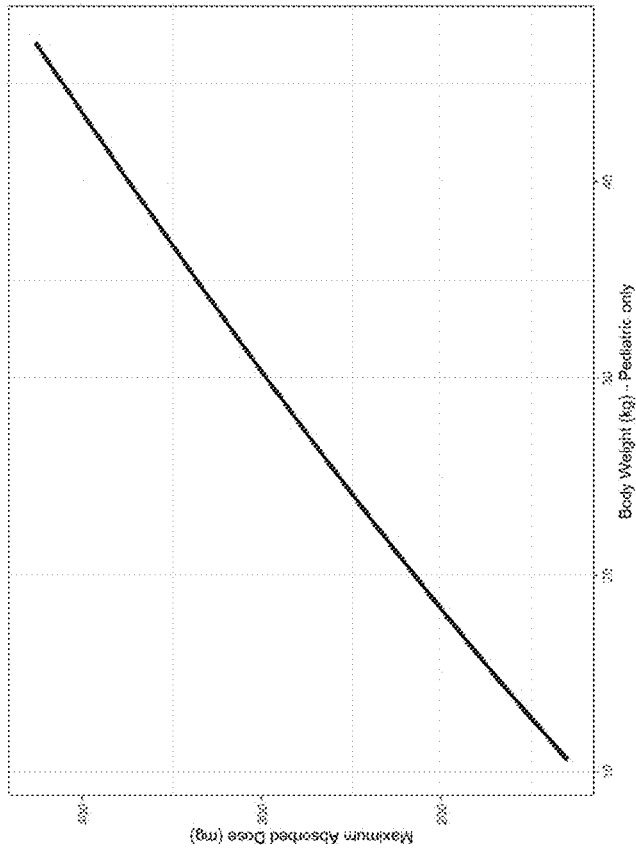

FIG. 11A is a table and FIG. 11B is a graph showing the results of a population pharmacokinetic analysis of ganaxolone in a population of pediatric subjects that included subjects with CDKL5 deficiency or other epilepsy disorders and healthy subjects.

4. DETAILED DESCRIPTION

This disclosure relates to methods for treating epilepsy disorders, including TSC, using a two phase titration of ganaxolone. The disclosed two phase titration mitigates or overcomes side effects associated with interactions between ganaxolone and CBD in patients who are receiving concomitant CBD treatment, including subjects who are concomitantly being administered CBE at a low dose (e.g., about 10 mg/kg/day or less) or at a high dose (e.g., greater than about 10 mg/kg/day). The disclosed two phase ganaxolone titration is also suitable for treating subjects who are not concomitantly being administered CBD.

In the first phase of the two phase titration ganaxolone is administered at a lower starting daily dose that has been previously used in clinical studies, and the dose in increased over a time until a dose that correlates with the absorption limit determined from population pharmacokinetic modeling in pediatric patients is achieved. Then the second phase begins and the dose of ganaxolone can be increased in larger increments until a target dose is achieved. The target dose is typically about 1200 mg/day to about 1800 mg/day and is achieved in about 5 weeks. A ganaxolone dose of about 1800 mg/day is typically the maximum dose administered. In prior clinical studies, the starting dose of ganaxolone was 450 mg/day or 18 mg/kg/day, which was administered for one week. The dose was then increased to 900 mg/day or 33 mg/kg/day for a week, then increased to 1350 mg/day or 48 mg/kg/day for a week, and then to the target dose of 1800 mg/day or 63 mg/kg/day.

Typically, in the two phase ganaxolone titration, the starting dose is about 90 mg/day to about 150 mg/day and is administered for about a week. The starting dose can be about 90 mg/day. The starting dose can be about 150 mg/day. Then, the dose is increased a first time and the first increased dose is administered to the subject for about a week. Typically, the first increased does is about double the starting dose and can be about 180 mg/day to about 300 mg/day. The first increased dose can be 180 mg/day. The first increased dose can be about 300 mg/day. Then, the dose is increased a second time and the second increased dose is administered to the subject for about a week. Typically, the second increased does is about double the first increased dose and can be about 360 mg/day to about 600 mg/day. The second increased dose can be 360 mg/day. The second increased dose can be about 600 mg/day. Then, the dose is increased a third time and the third increased dose is administered to the subject for about a week. Typically, the third increased does is about double the second increased dose and can be about 720 mg/day to about 1200 mg/day. The third increased dose can be 720 mg/day. The third increased dose can be about 1200 mg/day. Then, the dose is increased a fourth time to the target dose. Typically, the target dose is about 1200 mg/day to about 1800 mg/day. When the target dose is 1200 mg/day, the dose can be further increased up to about 1800 mg/day if desired or indicated for seizure control (and if the 1200 mg/day dose is well tolerated).

The two phase titration can include a starting dose of about 3 mg/kg/day to about 6 mg/kg/day that is administered for about a week. The starting dose can be about 3 mg/kg/day. The starting dose can be about 6 mg/kg/day. Then, the dose is increased a first time and the first increased dose is administered to the subject for about a week. Typically, the first increased does is about double the starting dose and can be about 6 mg/kg/day to about 12 mg/kg/day. The first increased dose can be 6 mg/kg/day. The first increased dose can be about 12 mg/kg/day. Then, the dose is increased a second time and the second increased dose is administered to the subject for about a week. Typically, the second increased does is about double the first increased dose and can be about 12 mg/kg/day to about 24 mg/kg/day. The second increased dose can be about 12 mg/kg/day. The second increased dose can be about 24 mg/kg/day. Then, the dose is increased a third time and the third increased dose is administered to the subject for about a week. Typically, the third increased does is about double the second increased dose and can be about 24 mg/kg/day to about 42 mg/kg/day. The third increased dose can be about 24 mg/kg/day. The third increased dose can be about 42 mg/kg/day. Then, the dose is increased a fourth time to the target dose. Typically, the target dose is about 42 mg/kg/day to about 63 mg/kg/day. When the target dose is 42 mg/kg/day, the dose can be further increased up to about 63 mg/kg/day if desired or indicated for seizure control (and if the 1200 mg/day dose is well tolerated).

In embodiments, the method comprises administering to a subject in need thereof ganaxolone in an amount of about 150 mg per day for about one week, followed by about 300 mg per day for about one week, followed by about 600 mg per day for about one week, followed by about 1,200 mg per day for about one week, followed by about 1,800 mg per day for the remaining treatment period. This method is preferably used to treat subjects that are not concomitantly being administered cannabidiol or subjects that are concomitantly being administered a low dose of cannabidiol (e.g., an amount of 10 mg/kg per day or less). This method can also be used to treat subjects who are concomitantly being administered high dose cannabidiol (e.g., an amount of >10 mg/kg per day).

In embodiments, the method comprises administering to a subject in need thereof ganaxolone in an amount up to about 90 mg per day for about a week, followed by about 180 mg per day for about one week, followed by about 360 mg per day for about one week, followed by about 720 mg per day for about one week, followed by about 1,200 mg per day for at least about 1 week. The method can further comprise administering ganaxolone in an amount of up to about 1,800 mg per day following administration of ganaxolone in an amount of about 1,200 mg per day for about one week. This method is preferably used to treat subjects who are concomitantly being administered a high dose of cannabidiol (e.g., 10 mg/kg per day or more).

A. Preferred Methods for Treating Patients Who are not Receiving Concomitant Treatment with CBD or are Receiving Concomitant Treatment with Low Dose CBD Certain methods described herein are preferred for treating patients who are not receiving concomitant treatment with CBD or are receiving concomitant treatment with low dose CBD (e.g., an amount of 10 mg CBD/kg per day or less). Such methods comprise administering to a subject in need thereof ganaxolone in an amount of up to about 150 mg per day for about one week, followed by up to about 300 mg per day for about one week, followed by up to about 600 mg per day for about one week, followed by up to about 1,200 mg per day for about one week, followed by about 1,200 mg per day up to about 1,800 mg per day for the remaining treatment period. This dosing regimen is preferred for subjects that are not concomitantly being administered cannabidiol or concomitantly being administered a low dose of cannabidiol (e.g., an amount of 10 mg/kg per day or less).

The method comprises administering an initial amount of ganaxolone of up to about 150 mg per day for about 1 week. The amount of ganaxolone initially administered can be about 90 mg per day, about 95 mg per day, about 100 mg per day, about 110 mg per day, about 120 mg per day, about 125 mg per day, about 130 mg per day, about 135 mg per day, about 140 mg per day, about 145 mg per day, about 150 mg per day, about 155 mg per day, or about 160 mg per day. It is preferred that the amount of ganaxolone administered is about 150 mg per day for about a week.

According to the preferred method, the dose of ganaxolone administered is then increased up to about 300 mg per day for about 1 week. For example, the amount of ganaxolone administered can be about 135 mg per day about 140 mg per day, about 145 mg per day, about 150 mg per day, about 155 mg per day, about 160 mg per day, about 170 mg per day, about 175 mg per day, about 180 mg per day, about 185 mg per day, about 190 mg per day, about 195 mg per day, about 200 mg per day, about 205 mg per day, about 210 mg per day, about 215 mg per day, about 220 mg per day, about 225 mg per day, about 230 mg per day, about 240 mg per day, about 250 mg per day, about 260 mg per day, about 270 mg per day, about 280 mg per day, about 290 mg per day, about 300 mg per day, about 310 mg per day, about 320 mg per day, about 330 mg per day, about 340 mg per day, or about 350 mg per day. It is preferred that the amount of ganaxolone administered is about 300 mg per day for about a week.

Following the preferred method, the dose of ganaxolone administered is then increased again up to about 600 mg per day for about one week. For example, the amount of ganaxolone administered can be about 270 mg per day, about 280 mg per day, about 290 mg per day, about 300 mg per day, about 310 mg per day, about 320 mg per day, about 330 mg per day, about 340 mg per day, about 350 mg per day, about 400 mg per day, about 450 mg per day, about 500 mg per day, about 550 mg per day, about 600 mg per day, about 610 mg per day, about 620 mg per day, about 630 mg per day, about 640 mg per day, or about 650 mg per day. It is preferred that the amount of ganaxolone administered is about 600 mg per day for about a week.

Following the preferred method, the dose of ganaxolone administered is a then increased again to up to about 1200 mg per day for about a week. For example, the amount of ganaxolone administered can be about 550 mg per day, about 600 mg per day, about 650 mg per day, about 700 mg per day, about 750 mg per day, about 800 mg per day, about 850 mg per day, about 900 mg per day, about 1000 mg per day, about 1100 mg per day, about 1150 mg per day, about 1200 mg per day, about 1210 mg per day, about 1220 mg per day, about 1230 mg per day, about 1240 mg per day, about 1250 mg per day, or about 1300 mg per day. It is preferred that the amount of ganaxolone administered is about 1200 mg per day for about a week.

Following the preferred method, the dose of ganaxolone administered can then be increased up to about 1800 mg per day for the remaining treatment period. For example, the amount of ganaxolone administered can be about 1000 mg per day, about 1100 mg per day, about 1200 mg per day, about 1250 mg per day, about 1300 mg per day, about 1350 mg per day, about 1400 mg per day, about 1450 mg per day, about 1500 mg per day, about 1550 mg per day, about 1600 mg per day, about 1650 mg per day, about 1700 mg per day, about 1750 mg per day, or about 1800 mg per day. Preferably the dose of ganaxolone that is administered for the remaining treatment period is between about 1200 mg/day and about 1800 mg/day, and more preferable is about 1800 mg/day.

The amount of ganaxolone administered can be weight based if desired, for example when a subject in need of treatment weights 40 kg or less, in particular 28 kg or less. Accordingly, the method can comprise administering to a subject in need thereof ganaxolone in an amount of up to about 6 mg/kg/day for about one week, followed by about up to about 12 mg/kg/day for about one week, followed by about 24 mg/kg/day for about one week, followed by about 42 mg/kg/day for about one week, followed by up to about 63 mg/kg/day for the remaining treatment period.

This preferred method comprises administering an initial amount of ganaxolone of up to about 6 mg/kg/day about 1 week. The amount of ganaxolone initially administered can be about 1 mg/kg/day, about 2 mg/kg/day, about 3 mg/kg/day, about 4 mg/kg/day, about 5 mg/kg/day, about 6 mg/kg/day, about 7 mg/kg/day, or about 8 mg/kg/day. It is preferred that about 6 mg/kg/day is administered. Following the preferred method, the amount of ganaxolone administered is then increased up to about 12 mg/kg/day for about a week. For example, the amount of ganaxolone administered can be about 7 mg/kg/day, about 8 mg/kg/day, about 9 mg/kg/day, about 10 mg/kg/day, about 11 mg/kg/day, about 12 mg/kg/day, about 13 mg/kg/day, or about 14 mg/kg/day. It is preferred that about 12 mg/kg/day is administered. Following the preferred method, the amount of ganaxolone administered is then increased up to about 24 mg/kg/day for about a week. For example, the amount of ganaxolone administered can be about 13 mg/kg/day, about 14 mg/kg/day, about 15 mg/kg/day, about 16 mg/kg/day, about 17 mg/kg/day, about 18 mg/kg/day, about 19 mg/kg/day, about 20 mg/kg/day, about 21 mg/kg/day, about 22 mg/kg/day, about 23 mg/kg/day, about 24 mg/kg/day, about 25 mg/kg/day, or about 26 mg/kg/day. Following the preferred method, the amount of ganaxolone administered is increased up to about 42 mg/kg/day for about one week. For example, the amount of ganaxolone administered can be up to about 26 mg/kg/day, about 27 mg/kg/day, about 28 mg/kg/day, about 29 mg/kg/day, about 30 mg/kg/day, about 31 mg/kg/day, about 32 mg/kg/day, about 33 mg/kg/day, about 34 mg/kg/day, about 35 mg/kg/day, about 36 mg/kg/day, about 37 mg/kg/day, about 38 mg/kg/day, about 39 mg/kg/day, about 40 mg/kg/day, about 41 mg/kg/day, about 42 mg/kg/day, about 43 mg/kg/day, or about 44 mg/kg/day. It is preferred that about 42 mg/kg/day is administered for about a week. Following the preferred method, the amount of ganaxolone administered is then increased and about 63 mg/kg/day is administered for the remaining treatment period. For example, about 43 mg/kg/day, about 44 mg/kg/day, about 45 mg/kg/day, about 46 mg/kg/day, about 47 mg/kg/day, about 48 mg/kg/day, about 49 mg/kg/day, about 50 mg/kg/day, about 51 mg/kg/day, about 52 mg/kg/day, about 53 mg/kg/day, about 54 mg/kg/day, about 55 mg/kg/day, about 56 mg/kg/day, about 57 mg/kg/day, about 58 mg/kg/day, about 59 mg/kg/day, about 60 mg/kg/day, about 61 mg/kg/day, about 62 mg/kg/day, or about 63 mg/kg/day can be administered. It is preferred that about 63 mg/kg/day is administered for the remaining treatment period.

A skilled clinician will understand that the amount of ganaxolone administered can be adjusted based on subject tolerability and need for additional seizure control, but that the amount administered preferably does not exceed 1800 mg/day.

Generally, ganaxolone is administered (e.g., orally) at least one or more times a day. For instance, one time a day, two times a day, three times a day, four times a day, five times a day, six times a day, seven times a day, eight times a day or more. Three times a day is preferable, although if needed or desirable ganaxolone can be administered more than three times or less than three times based on subject tolerability and need for additional seizure control.

For instance, the methods disclosed herein can comprise administering ganaxolone in an amount of up to about 50 mg administered three times a day for about a week (about 150 mg/day), followed by about 100 mg administered three times a day for about a week (about 300 mg/day), followed by up to about 200 mg administered three times a day for amount a week (about 600 mg/day), followed by about 400 mg administered three times a day for about a week (about 1200 mg/day), followed by about 600 mg administered three times a day (about 1800 mg/day) for the remaining treatment period.

For instance, the methods disclosed herein can comprise administering ganaxolone (e.g., to a subject that weighs less than 40 kg, in particular 28 kg or less) in an amount of up to about 2 mg/kg three times a day for about a week, followed by about 4 mg/kg three times a day for about a week, followed by about 8 mg/kg three times a day for about a week, followed by about 14 mg/kg three times a day for about a week, followed by up to about 21 mg/kg three times a day for about a week.

Generally, each dose of ganaxolone is administered for up about a week (e.g., about 7 days). While it is preferred that each dose of ganaxolone is administered for about one week, there can be some variability based on, for example, the subject's metabolism, age, duration of seizure, severity of seizure, and tolerability of ganaxolone. For instance, the duration each dose is administered can be less than one week or longer than one week. For instance each dose of ganaxolone can be administered for about 1 day, about 2 days, about 3 days, about 4 days, about 5 days, about 6 days, about 7 days, about 8 days, about 9 days, about 10 days, about 11 days, about 12 days, about 13 days, about 14 days, about 15, about 16 days, about 17 days, about 18 days, about 19 days, about 20 days, about 21 days or longer.

The titration period is usually at least about 4 weeks, reaching the target dose at about week 5. The titration period may be shorter or longer, based upon the clinical judgement of a skilled clinician. Typically, once the target dose of ganaxolone is administered the subject continues receiving the target dose or up to about the maximal dose of ganaxolone (e.g., 1800 mg per day or 63/mg/kg) for continued suppression and management of seizures. For example, the treatment period can be about 2 months, about 3 months, about 4 months, about 5 months, about 6 months, about 7 months, about 8 months, about 9 months, about 10 months, about 11 months, about 1 year, about 2 years, about 3 years, about 4 years, about 5 years, about 6 years, about 7 years, about 8 years, about 9 years, about 10 years or longer.

B. Preferred Methods for Treating Patients Who are Receiving Concomitant Treatment with High Dose CBD Certain methods described herein are preferred for treating patients who are receiving concomitant treatment with high dose CBD (e.g., 10 mg/kg per day or more). Such methods comprise administering to a subject in need thereof ganaxolone in an amount up to about 90 mg per day for about a week, followed by up to about 180 mg per day for about one week, followed by about up to 360 mg per day for about one week, followed by about up to 720 mg per day for about one week, followed by about up to 1,200 mg per day for at least about 1 week. Preferably, the titration of ganaxolone stops when the dose reaches about 1,200 mg per day, and that dose is then administered for the remainder of the treatment period. However, for subjects that reach the 1,200 mg/day target dose of ganaxolone, the dose may be increased further up to about 1,800 me per day based on tolerability, and if desired or indicated for seizure control. The amount of ganaxolone can be increased up to about 1,800 mg per day following administration of ganaxolone in an amount of about 1,200 mg per day for about one week or longer.

The preferred method comprises administering an initial amount of ganaxolone of up to about 90 mg per day for about 1 week. The amount of ganaxolone initially administered can be about 45 mg per day, about 50 mg per day, about 55 mg per day, about 60 mg per day, about 65 mg per day, about 70 mg per day, 75 mg per day, about 80 mg per day, about 85 mg per day, about 90 mg per day, about 95 mg per day, about 100 mg per day, or about 110 mg per day. It is preferred that the amount of ganaxolone administered is about 90 mg per day for about a week.

Following the preferred method, the amount of ganaxolone administered is then increased up to about 180 mg per day for about 1 week. For example, the amount of ganaxolone administered can be about 135 mg per day about 140 mg per day, about 145 mg per day about 150 mg per day, about 155 mg per day, about 160 mg per day, about 170 mg per day, about 175 mg per day, about 180 mg per day, about 185 mg per day, about 190 mg per day, about 195 mg per day, or about 200 mg per day. It is preferred that the amount of ganaxolone administered is about 180 mg per day for about a week.

Following the preferred method, the amount of ganaxolone administered is then increased up to about 360 mg per day for about one week. For example, the amount of ganaxolone administered can be about 270 mg per day, about 280 mg per day, about 290 mg per day, about 300 mg per day, about 310 mg per day, about 320 mg per day, about 330 mg per day, about 340 mg per day, about 350 mg per day, about 360 mg per day, about 370 mg per day, about 380 mg per day, about 390 mg per day, or about 400 mg per day. It is preferred that the amount of ganaxolone administered is about 360 mg per day for about a week.

Following the preferred method, the amount of ganaxolone administered is then increased up to about 720 mg per day for about a week. For example, the amount of ganaxolone administered can be about 550 mg per day, 560 mg per day, 570 mg per day, 580 mg per day, 590 mg per day, about 600 mg per day, 610 mg per day, 620 mg per day, 630 mg per day, 640 mg per day, about 650 mg per day, 660 mg per day, 670 mg per day, 680 mg per day, 690 mg per day, about 700 mg per day, 720 mg per day, 730 mg per day, 740 mg per day, or about 750 mg per day. It is preferred that the amount of ganaxolone administered is about 720 mg per day for about a week.

Following the preferred method, the amount of ganaxolone administered is then increased up to about 1200 mg per day for at least about one week. For example, the amount of ganaxolone administered can be about 900 mg per day, about 950 mg per day, about 1000 mg per day, 1010 mg per day, 1020 mg per day, 1030 mg per day, 1040 mg per day, 1050 mg per day, 1060 mg per day, 1070 mg per day, 1080 mg per day, 1090 mg per day, about 1100 mg per day, about 1200 mg per day, about 1250 mg per day, about 1300 mg per day, about 1350 mg per day, or about 1400 mg per day. It is preferred that the amount of ganaxolone administered is about 1200 mg per day for about a week. Preferably, the titration of ganaxolone stops when the dose reaches about 1,200 mg per day, and that dose is then administered for the remainder of the treatment period.

The amount of ganaxolone can be increased up to about 1,800 mg per day following administration of ganaxolone in an amount of about 1,200 mg per day for about one week or longer. For instance, the amount of ganaxolone can be increased up to about 1250 mg per day, about 1300 mg per day, about 1350 mg per day, about 1400 mg per day, about 1450 mg per day, about 1500 mg per day, about 1550 mg per day, about 1600 mg per day, about 1650 mg per day, about 1700 mg per day about 1750 mg per day, or about 1,800 mg per day.

The amount of ganaxolone administered can be weight based if desired, for example when a subject in need of treatment weights 40 kg or less, in particular 28 kg or less. Accordingly, the method can comprise administering to a subject in need thereof ganaxolone in an amount of up to about 3 mg/kg/day for about one week, followed by about up to about 6 mg/kg/day for about one week, followed by about 12 mg/kg/day for about one week, followed by about 24 mg/kg/day for about one week, followed by up to about 42 mg/kg/day for the remaining treatment period. The amount of ganaxolone can be increased up to about 63 mg/kg/day following administration of ganaxolone in an amount of about 42 mg/kg/day for about one week or longer. For instance, the amount of ganaxolone can be increased up about 43 mg/kg/day, about 44 mg/kg/day, about 45 mg/kg/day, about 46 mg/kg/day, about 47 mg/kg/day, about 48 mg/kg/day, about 49 mg/kg/day, about 50 mg/kg/day, about 51 mg/kg/day, about 52 mg/kg/day, about 53 mg/kg/day, about 54 mg/kg/day, about 55 mg/kg/day, about 56 mg/kg/day, about 57 mg/kg/day, about 58 mg/kg/day, about 59 mg/kg/day, about 60 mg/kg/day, about 61 mg/kg/day, about 62 mg/kg/day, or about 63 mg/kg/day.

The preferred method comprises administering an initial amount of ganaxolone of up to about 3 mg/kg/day about 1 week. The amount of ganaxolone initially administered can be about 0.5 mg/kg/day, about 1 mg/kg/day, about 2 mg/kg/day, or about 3 mg/kg/day. It is preferred that about 3 mg/kg/day is administered. Following, the amount of ganaxolone administered is up to about 6 mg/kg/day. The amount of ganaxolone initially administered can be about 1 mg/kg/day, about 2 mg/kg/day, about 3 mg/kg/day, about 4 mg/kg/day, about 5 mg/kg/day, about 6 mg/kg/day, about 7 mg/kg/day, or about 8 mg/kg/day. It is preferred that about 6 mg/kg/day is administered.

Following the preferred method, the amount of ganaxolone administered is then increased up to about 12 mg/kg/day for about a week. For example, the amount of ganaxolone administered can be about 7 mg/kg/day, about 8 mg/kg/day, about 9 mg/kg/day, about 10 mg/kg/day, about 11 mg/kg/day, about 12 mg/kg/day, about 13 mg/kg/day, or about 14 mg/kg/day. It is preferred that about 12 mg/kg/day is administered.

Following the preferred method, the amount of ganaxolone administered is then increased up to about 24 mg/kg/day for about a week. For example, the amount of ganaxolone administered can be about 13 mg/kg/day, about 14 mg/kg/day, about 15 mg/kg/day, about 16 mg/kg/day, about 17 mg/kg/day, about 18 mg/kg/day, about 19 mg/kg/day, about 20 mg/kg/day, about 21 mg/kg/day, about 22 mg/kg/day, about 23 mg/kg/day, about 24 mg/kg/day, about 25 mg/kg/day, or about 26 mg/kg/day.

Following the preferred method, the amount of ganaxolone administered is then increased up to about 42 mg/kg/day for about one week. For example, the amount of ganaxolone administered can be up to about 26 mg/kg/day, about 27 mg/kg/day, about 28 mg/kg/day, about 29 mg/kg/day, about 30 mg/kg/day, about 31 mg/kg/day, about 32 mg/kg/day, about 33 mg/kg/day, about 34 mg/kg/day, about 35 mg/kg/day, about 36 mg/kg/day, about 37 mg/kg/day, about 38 mg/kg/day, about 39 mg/kg/day, about 40 mg/kg/day, about 41 mg/kg/day, about 42 mg/kg/day, about 43 mg/kg/day, or about 44 mg/kg/day. It is preferred that about 42 mg/kg/day is administered for about a week.

The amount of ganaxolone can be increased up to about 63 mg/kg/day following administration of ganaxolone in an amount of about 42 mg/kg/day for about one week or longer. For instance, the amount of ganaxolone can be increased up about 43 mg/kg/day, about 44 mg/kg/day, about 45 mg/kg/day, about 46 mg/kg/day, about 47 mg/kg/day, about 48 mg/kg/day, about 49 mg/kg/day, about 50 mg/kg/day, about 51 mg/kg/day, about 52 mg/kg/day, about 53 mg/kg/day, about 54 mg/kg/day, about 55 mg/kg/day, about 56 mg/kg/day, about 57 mg/kg/day, about 58 mg/kg/day, about 59 mg/kg/day, about 60 mg/kg/day, about 61 mg/kg/day, about 62 mg/kg/day, or about 63 mg/kg/day.

A skilled clinician will understand that the amount of ganaxolone administered can be adjusted based on subject tolerability and need for additional seizure control, but that the amount administered preferably does not exceed 1800 mg/day.

Generally, ganaxolone is administered (e.g., orally) at least one or more times a day. For instance, one time a day, two times a day, three times a day, four times a day, five times a day, six times a day, seven times a day, eight times a day or more. Three times a day is preferable, although if needed or desirable ganaxolone can be administered more than three times or less than three times based on subject tolerability and need for additional seizure control.

For instance, the methods disclosed herein can comprise administering ganaxolone in an amount of up to about 30 mg administered three times a day for about a week, followed by about 60 mg administered three times a day for about a week, followed by up to about 120 mg administered three times a day for amount a week, followed by about 240 mg administered three times a day for about a week, followed by about 400 mg administered three times a day for the remaining treatment period.

For instance, in subjects weighing less than 40 kg, in particular 28 kg or less, the methods disclosed herein can comprise administering ganaxolone in an amount of up to about 1 mg/kg three times a day for about a week, followed by about 2 mg/kg three times a day for about a week, followed by about 4 mg/kg three times a day for about a week, followed by about 8 mg/kg three times a day for about a week, followed by up to about 14 mg/kg three times a day for about a week.

Generally, each dose of ganaxolone is administered for up about a week (e.g., about 7 days). While it is preferred that each dose of ganaxolone is administered for about one week, there can be some variability based on, for example, the subject's metabolism, age, duration of seizure, severity of seizure, and tolerability of ganaxolone. For instance, the duration each dose is administered can be less than one week or longer than one week. For instance each dose of ganaxolone can be administered for about 1 day, about 2 days, about 3 days, about 4 days, about 5 days, about 6 days, about 7 days, about 8 days, about 9 days, about 10 days, about 11 days, about 12 days, about 13 days, about 14 days, about 15, about 16 days, about 17 days, about 18 days, about 19 days, about 20 days, about 21 days or longer.

The titration period is usually at least about 4 weeks, reaching the target dose at about week 5. Typically, once the target dose of ganaxolone is administered the subject continues receiving the target dose or up to about the maximal dose of ganaxolone (e.g., 1800 mg per day or 63/mg/kg) for continued suppression and management of seizures. For example, the treatment period can be about 1 month, about 2 months, about 3 months, about 4 months, about 5 months, about 6 months, about 7 months, about 8 months, about 9 months, about 10 months, about 11 months, about 1 year, about 2 years, about 3 years, about 4 years, about 5 years, about 6 years, about 7 years, about 8 years, about 9 years, about 10 years or longer.

C. Subjects to be Treated

The methods disclosed herein are suitable to treat any form of seizure or epilepsy disorder such as, focal seizures (e.g. temporal lobe seizures, frontal lobe seizures, occipital lobe seizures, or parietal lobe seizures), generalized seizures (e.g., absence seizures, myoclonic seizures, generalized tonic-clonic seizures), progressive myoclonic epilepsy, reflex epilepsy, Landau-Kleffner Syndrome, Ohtahara syndrome, Rasmussen's syndrome, infantile spasms (or West syndrome), Lennox-Gastaut syndrome (LGS), Rett syndrome, Dravet syndrome, Doose syndrome, CDKL5 deficiency disorder, intractable childhood epilepsy (ICE), childhood absence epilepsy (CAE), juvenile myoclonic epilepsy (JME), essential tremor, acute repetitive seizures, benign rolandic epilepsy, status epilepticus, refractory status epilepticus, super-refractory status epilepticus, PCDH19 pediatric epilepsy, increased seizure activity or breakthrough seizures (increased seizure activity; also called serial or cluster seizures), infantile spasms, Angleman's syndrome, Aicardi syndrome, and tuberous sclerosis complex (TSC). The methods can be used to treat seizures associated with any of the forgoing, such as seizures associated with TSC, seizures associated with CDKL5 deficiency disorder (CDD), and seizures associated with any of Landau-Kleffner Syndrome, Ohtahara syndrome, Rasmussen's syndrome, West syndrome, Lennox-Gastaut syndrome (LGS), Rett syndrome, Dravet syndrome, Doose syndrome, intractable childhood epilepsy (ICE), childhood absence epilepsy (CAE), juvenile myoclonic epilepsy (JME), essential tremor, benign rolandic epilepsy, status epilepticus, refractory status epilepticus, super-refractory status epilepticus, PCDH19 pediatric epilepsy, Angleman's syndrome, and Aicardi syndrome.

The methods disclosure herein are particularly suitable for treating tuberous sclerosis complex (TSC), Dravet syndrome, and Lennox-Gastaut syndrome. The methods disclosure herein are particularly suitable for treating seizures associated with tuberous sclerosis complex (TSC), seizures associated with Dravet syndrome, and seizures associated with Lennox-Gastaut syndrome. The methods disclosure herein are particularly suitable for treating CDD. The methods disclosure herein are particularly suitable for treating seizures associated with CDD.

The methods disclosed herein are preferably used for treating TSC. The methods can be used to treat any form of TSC-related epilepsy, for example, but are not limited to, infantile spasms, focal motor seizures without impairment of consciousness or awareness, focal seizures with impairment of consciousness or awareness, focal seizures evolving to bilateral, tonic-clonic convulsive seizures, and generalized seizures motor seizures including tonic-clonic, bilateral tonic, bilateral clonic, atonic/drop seizures that are countable, myoclonic seizures, or epileptic seizures.

Treatment according to the methods of this disclosure typically results in a reduction in seizure frequencies relative to baseline seizure frequency. Baseline seizure frequency can be the frequency of seizure experienced by the subject in the about 4 weeks prior to the start of therapy using the methods disclosed herein. Baseline seizure frequency can be the frequency of seizure experience by the subject over an about 4 week period following treatment with the target dose according to this disclosure relative to frequency of seizure in subjects treated with placebo. For example, treatment according to this disclosure can reduce seizure frequencies by at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 99% relative to baseline.

D. Ganaxolone Formulations

Any desired formulation that comprise a therapeutically effective amount of ganaxolone can be administered according to the methods disclosed herein.

The formulation is preferably an oral formulation of ganaxolone. In certain embodiments, a liquid formulation as described and prepared in U.S. Pat. No. 8,022,054, entitled "Liquid Ganaxolone Formulations and Methods for the Making and Use Thereof", hereby incorporated by reference in its entirety, is used. The oral liquid (e.g., suspension) formulation of ganaxolone may be prepared using any suitable methods.

As described in U.S. Pat. No. 8,022,054, the liquid formulation may be an aqueous dispersion of stabilized particles comprising ganaxolone, a hydrophilic polymer, a wetting agent, and an effective amount of a complexing agent that stabilizes particle growth after an initial particle growth and endpoint is reached, the complexing agent selected from the group of small organic molecules having a molecular weight less than 550 and containing a moiety selected from the group consisting of a phenol moiety, an aromatic ester moiety and an aromatic acid moiety, wherein the stabilized particles have a volume weighted median diameter (D50) of the particles from about 50 nm to about 500 nm, the complexing agent being present in an amount from about 0.05% to about 5%, w/w based on the weight of particles, the particles dispersed in an aqueous solution which further contains at least two preservatives in an amount sufficient to inhibit microbial growth. The hydrophilic polymer may be in an amount from about 3% to about 50%, w/w, based on the weight of the solid particles. The wetting agent may be an amount from about 0.01% to about 10%, w/w, based on the weight of the solid particles. Ganaxolone may be in an amount from about 10% to about 80% (and in certain embodiments form about 50% to about 80%) based on the weight of the stabilized particles. The stabilized particles may exhibit an increase in volume weighted median diameter (D50) of not more than about 150% when the particles are dispersed in simulated gastric fluid (SGF) or simulated intestinal fluid (SIF) at a concentration of 0.5 to 1 mg ganaxolone/mL and placed in a heated bath at 36° to 38° C. for 1 hour as compared to the D50 of the stabilized particles when the particles are dispersed in distilled water under the same conditions, wherein the volume weighted median diameter (D50) of the stabilized particles dispersed in SGF or SIF is less than about 750 nm. The stabilized particles may exhibit an increase in volume weighted median diameter (D50) of not more than about 150% when the formulation is dispersed in 15 mL of SGF or SIF at a concentration of 0.5 to 1 mg ganaxolone/mL as compared to the D50 of the stabilized particles when the particles are dispersed in distilled water under the same conditions, wherein the volume weighted median diameter (D50) of the stabilized particles dispersed in SGF or SIF is less than about 750 nm.

The complexing agent can be any molecule with a lipophilic core and hydrophilic outer shell capable of solubilizing ganaxolone. In certain embodiments, complexing agent can be a substance containing a phenol moiety, an aromatic ester moiety or an aromatic acid moiety. In certain embodiments, complexing agents are selected from the group consisting of parabens, organic acids, carboxylic acids, aromatic acids, aromatic esters, acid salts of amino acids, methyl anthranilate, sodium metabisulphite, ascorbic acid and its derivatives, malic acid, isoascorbic acid, citric acid, tartaric acid, sodium sulphite, sodium bisulphate, tocopherol, water- and fat-soluble derivatives of tocopherol, sulphites, bisulphites and hydrogen sulphites, para-aminobenzoic acid and esters, 2,6-di-t-butyl-alpha-dimethylamino-p-cresol, t-butylhydroquinone, di-t-amylhydroquinone, di-t-butylhydroquinone, butylhydroxytoluene (BHT), butylhydroxyanisole (BHA), pyrocatechol, pyrogallol, propyl/gallate, nordihydroguaiaretic acid, phosphoric acids, sorbic and benzoic acids, esters, ascorbyl palmitate, derivatives and isomeric compounds thereof, pharmaceutically acceptable salts thereof, and mixtures thereof. In certain embodiments, the complexing agent is selected from the group consisting of a paraben, benzoic acid, phenol, sodium benzoate, methyl anthranilate, and the like. The hydrophilic polymer may be a cellulosic polymer, a vinyl polymer and mixtures thereof. The cellulosic polymer may be a cellulose ether, e.g., hydroxypropymethylcellulose. The vinyl polymer may be polyvinyl alcohol, e.g., vinyl pyrrolidone/vinyl acetate copolymer (S630). The wetting agent may be sodium lauryl sulfate, a pharmaceutically acceptable salt of docusate, and mixtures thereof. The aqueous dispersion may further comprise a sweetener, e.g., sucralose. In certain embodiments, the preservative is selected from the group consisting of potassium sorbate, methylparaben, propylparaben, benzoic acid, butylparaben, ethyl alcohol, benzyl alcohol, phenol, benzalkonium chloride, and mixtures of any of the foregoing.

In some embodiments, liquid ganaxolone formulations comprising the ganaxolone particles described herein and at least one dispersing agent or suspending agent for oral administration to a subject are used. The ganaxolone formulation may be a powder and/or granules for suspension, and upon admixture with water, a substantially uniform suspension is obtained. As described herein, the aqueous dispersion can comprise amorphous and non-amorphous ganaxolone particles of consisting of multiple effective particle sizes such that ganaxolone particles having a smaller effective particle size are absorbed more quickly and ganaxolone particles having a larger effective particle size are absorbed more slowly. In certain embodiments, the aqueous dispersion or suspension used in the methods disclosed herein is an immediate release formulation. In another embodiment, an aqueous dispersion comprising amorphous ganaxolone particles is formulated such that about 50% of the ganaxolone particles are absorbed within about 3 hours after administration and about 90% of the ganaxolone particles are absorbed within about 10 hours after administration. In other embodiments, addition of a complexing agent to the aqueous dispersion results in a larger span of ganaxolone containing particles to extend the drug absorption phase such that 50-80% of the particles are absorbed in the first 3 hours and about 90% are absorbed by about 10 hours.

A suspension is "substantially uniform" when it is mostly homogenous, that is, when the suspension is composed of approximately the same concentration of ganaxolone at any point throughout the suspension. Preferred embodiments are those that provide concentrations essentially the same (within 15%) when measured at various points in a ganaxolone aqueous oral formulation after shaking. Especially preferred are aqueous suspensions and dispersions, which maintain homogeneity (up to 15% variation) when measured 2 hours after shaking. The homogeneity should be determined by a sampling method consistent with regard to determining homogeneity of the entire composition. In one embodiment, an aqueous suspension can be re-suspended into a homogenous suspension by physical agitation lasting less than 1 minute. In another embodiment, an aqueous suspension can be re-suspended into a homogenous suspension by physical agitation lasting less than 45 seconds. In yet another embodiment, an aqueous suspension can be re-suspended into a homogenous suspension by physical agitation lasting less than 30 seconds. In still another embodiment, no agitation is necessary to maintain a homogeneous aqueous dispersion.

In some embodiments, ganaxolone formulations are powders for aqueous dispersion and comprise stable ganaxolone particles having an effective particle size by weight of less than 500 nm formulated with ganaxolone particles having an effective particle size by weight of greater than 500 nm. In such embodiments, the formulations have a particle size distribution wherein about 10% to about 100% of the ganaxolone particles by weight are between about 75 nm and about 500 nm, about 0% to about 90% of the ganaxolone particles by weight are between about 150 nm and about 400 nm, and about 0% to about 30% of the ganaxolone particles by weight are greater than about 600 nm. The ganaxolone particles describe herein can be amorphous, semi-amorphous, crystalline, semi-crystalline, or mixture thereof.

In one embodiment, the aqueous suspensions or dispersions described herein comprise ganaxolone particles or ganaxolone complex at a concentration of about 20 mg/ml to about 150 mg/ml of suspension. In another embodiment, the aqueous oral dispersions described herein comprise ganaxolone particles or ganaxolone complex particles at a concentration of about 25 mg/ml to about 75 mg/ml of solution. In yet another embodiment, the aqueous oral dispersions described herein comprise ganaxolone particles or ganaxolone complex at a concentration of about 50 mg/ml of suspension. The aqueous dispersions described herein are especially beneficial for the administration of ganaxolone to infants (less than 2 years old), children under 10 years of age and any patient group that is unable to swallow or ingest solid oral dosage forms.

Liquid ganaxolone formulation for oral administration can be aqueous suspensions selected from the group including, but not limited to, pharmaceutically acceptable aqueous oral dispersions, emulsions, solutions, and syrups. See, e.g., Singh et al., Encyclopedia of Pharmaceutical Technology, 2nd Ed., pp. 754-757 (2002). In addition to ganaxolone particles, the liquid dosage forms may comprise additives, such as: (a) disintegrating agents; (b) dispersing agents; (c) wetting agents; (d) at least one preservative, (e) viscosity enhancing agents, (f) at least one sweetening agent, (g) at least one flavoring agent, (h) a complexing agent, and (i) an ionic dispersion modulator. In some embodiments, the aqueous dispersions can further comprise a crystalline inhibitor.

Examples of disintegrating agents for use in the aqueous suspensions and dispersions include, but are not limited to, a starch, e.g., a natural starch such as corn starch or potato starch, a pregelatinized starch such as National 1551 or AMIJELE®, or sodium starch glycolate such as PROMOGEL® or EXPLOTAB®; a cellulose such as a wood product, microcrystalline cellulose, e.g., AVICEL®, AVICEL® PH101, AVICEL® PH102, AVICEL® PH105, ELCEMA® P100, EMCOCEL®, VIVACEL®, MING TIA®, and SOLKA-FLOC®, methylcellulose, croscarmellose, or a cross-linked cellulose, such as cross-linked sodium carboxymethylcellulose (AC-DI-SOL®), cross-linked carboxymethylcellulose, or cross-linked croscarmellose; a cross-linked starch such as sodium starch glycolate; a cross-linked polymer such as crospovidone; a cross-linked polyvinylpyrrolidone; alginate such as alginic acid or a salt of alginic acid such as sodium alginate; a clay such as VEEGUM® HV (magnesium aluminum silicate); a gum such as agar, guar, locust bean, Karaya, pectin, or tragacanth; sodium starch glycolate; bentonite; a natural sponge; a surfactant; a resin such as a cation-exchange resin; citrus pulp; sodium lauryl sulfate; sodium lauryl sulfate in combination starch; and the like.

In some embodiments, the dispersing agents suitable for the aqueous suspensions and dispersions described herein are known in the art and include, for example, hydrophilic polymers, electrolytes, TWEEN® 60 or 80, PEG, polyvinylpyrrolidone (PVP; commercially known as PLASDONE®), and the carbohydrate-based dispersing agents such as, for example, hydroxypropylcellulose and hydroxypropylcellulose ethers (e.g., HPC, HPC-SL, and HPC-L), hydroxypropylmethylcellulose and hydroxypropylmethylcellulose ethers (e.g. HPMC K100, HPMC K4M, HPMC K15M, and HPMC K100M), carboxymethylcellulose sodium, methylcellulose, hydroxyethylcellulose, hydroxypropylmethylcellulose phthalate, hydroxypropylmethylcellulose acetate stearate, noncrystalline cellulose, magnesium aluminum silicate, triethanolamine, polyvinyl alcohol (PVA), polyvinylpyrrolidone/vinyl acetate copolymer (PLASDONE®, e.g., S-630), 4-(1,1,3,3-tetramethylbutyl)-phenol polymer with ethylene oxide and formaldehyde (also known as tyloxapol), poloxamers (e.g., Pluronics F68®, F88®, and F108®, which are block copolymers of ethylene oxide and propylene oxide); and poloxamines (e.g., Tetronic 9080, also known as Poloxamine 9080, which is a tetrafunctional block copolymer derived from sequential addition of propylene oxide and ethylene oxide to ethylenediamine (BASF Corporation, Parsippany, N.J.)). In other embodiments, the dispersing agent is selected from a group not comprising one of the following agents: hydrophilic polymers; electrolytes; TWEEN® 60 or 80; PEG; polyvinylpyrrolidone (PVP); hydroxypropylcellulose and hydroxypropyl cellulose ethers (e.g., HPC, HPC-SL, and HPC-L); hydroxypropyl methylcellulose and hydroxypropyl methylcellulose ethers (e.g. HPMC K100, HPMC K4M, HPMC K15M, HPMC K100M, and PHARMACOAT® USP 2910 (Shin-Etsu)); carboxymethylcellulose sodium; methylcellulose; hydroxyethylcellulose; hydroxypropylmethyl-cellulose phthalate; hydroxypropylmethyl-cellulose acetate stearate; non-crystalline cellulose; magnesium aluminum silicate; triethanolamine; polyvinyl alcohol (PVA); 4-(1,1,3,3-tetramethylbutyl)-phenol polymer with ethylene oxide and formaldehyde; poloxamers (e.g., PLURONICS F68®, F88®, and F108®, which are block copolymers of ethylene oxide and propylene oxide); or poloxamines (e.g., TETRONIC 908®, also known as Poloxamine 908%).

Wetting agents (including surfactants) suitable for the aqueous suspensions and dispersions described herein are known in the art and include, but are not limited to, acetyl alcohol, glycerol monostearate, polyoxyethylene sorbitan fatty acid esters (e.g., the commercially available TWEENs® such as e.g., TWEEN 20® and TWEEN 80) (ICI Specialty Chemicals)), and polyethylene glycols (e.g., CARBOWAXs 3350® and 1450®, and CARPOOL 934® (Union Carbide)), oleic acid, glyceryl monostearate, sorbitan monooleate, sorbitan monolaurate, triethanolamine oleate, polyoxyethylene sorbitan monooleate, polyoxyethylene sorbitan monolaurate, sodium oleate, sodium lauryl sulfate, sodium docusate, triacetin, vitamin E TPGS, sodium taurocholate, simethicone, phosphotidylcholine and the like.

Suitable preservatives for the aqueous suspensions or dispersions described herein include, for example, potassium sorbate, parabens (e.g., methylparaben and propylparaben) and their salts, benzoic acid and its salts, other esters of parahydroxybenzoic acid such as butylparaben, alcohols such as ethyl alcohol or benzyl alcohol, phenolic compounds such as phenol, or quaternary compounds such as benzalkonium chloride. Preservatives, as used herein, are incorporated into the dosage form at a concentration sufficient to inhibit microbial growth. In one embodiment, the aqueous liquid dispersion can comprise methylparaben and propylparaben in a concentration ranging from about 0.01% to about 0.3% methylparaben by weight to the weight of the aqueous dispersion and 0.005% to 0.03% propylparaben by weight to the total aqueous dispersion weight. In yet another embodiment, the aqueous liquid dispersion can comprise methylparaben 0.05 to about 0.1 weight % and propylparaben from 0.01-0.02 weight % of the aqueous dispersion.

Suitable viscosity enhancing agents for the aqueous suspensions or dispersions described herein include, but are not limited to, methyl cellulose, xanthan gum, carboxymethylcellulose, hydroxypropyl cellulose, hydroxypropylmethyl cellulose, Plasdone® S-630, carbomer, polyvinyl alcohol, alginates, acacia, chitosans and combinations thereof. The concentration of the viscosity enhancing agent will depend upon the agent selected and the viscosity desired.

Examples of natural and artificial sweetening agents suitable for the aqueous suspensions or dispersions described herein include, for example, acacia syrup, acesulfame K, alitame, anise, apple, aspartame, banana, Bavarian cream, berry, black currant, butterscotch, calcium citrate, camphor, caramel, cherry, cherry cream, chocolate, cinnamon, bubble gum, citrus, citrus punch, citrus cream, cotton candy, cocoa, cola, cool cherry, cool citrus, cyclamate, cylamate, dextrose, eucalyptus, eugenol, fructose, fruit punch, ginger, glycyrrhetinate, glycyrrhiza (licorice) syrup, grape, grapefruit, honey, isomalt, lemon, lime, lemon cream, monoammonium glyrrhizinate (MAGNASWEET®), maltol, mannitol, maple, marshmallow, menthol, mint cream, mixed berry, neohesperidine DC, neotame, orange, pear, peach, peppermint, peppermint cream, PROSWEET®. Powder, raspberry, root beer, rum, saccharin, safrole, sorbitol, spearmint, spearmint cream, strawberry, strawberry cream, stevia, sucralose, sucrose, sodium saccharin, saccharin, aspartame, acesulfame potassium, mannitol, talin, sucralose, sorbitol, Swiss cream, tagatose, tangerine, thaumatin, tutti fruitti, vanilla, walnut, watermelon, wild cherry, wintergreen, xylitol, or any combination of these flavoring ingredients, e.g., anise-menthol, cherry-anise, cinnamon-orange, cherry-cinnamon, chocolate-mint, honey-lemon, lemon-lime, lemon-mint, menthol-eucalyptus, orange-cream, vanilla-mint, and mixtures thereof. In one embodiment, the aqueous liquid dispersion can comprise a sweetening agent or flavoring agent in a concentration ranging from about 0.0001% to about 10.0% the weight of the aqueous dispersion. In another embodiment, the aqueous liquid dispersion can comprise a sweetening agent or flavoring agent in a concentration ranging from about 0.0005% to about 5.0% wt % of the aqueous dispersion. In yet another embodiment, the aqueous liquid dispersion can comprise a sweetening agent or flavoring agent in a concentration ranging from about 0.0001% to 0.1 wt %, from about 0.001% to about 0.01 weight %, or from 0.0005% to 0.004% of the aqueous dispersion.

In addition to the additives listed above, the liquid ganaxolone formulations can also comprise inert diluents commonly used in the art, such as water or other solvents, solubilizing agents, and emulsifiers.

In some embodiments, the ganaxolone formulations can be self-emulsifying drug delivery systems (SEDDS). Emulsions are dispersions of one immiscible phase in another, usually in the form of droplets. Generally, emulsions are created by vigorous mechanical dispersion. SEDDS, as opposed to emulsions or microemulsions, spontaneously form emulsions when added to an excess of water without any external mechanical dispersion or agitation. An advantage of SEDDS is that only gentle mixing is required to distribute the droplets throughout the solution. Additionally, water or the aqueous phase can be added just prior to administration, which ensures stability of an unstable or hydrophobic active ingredient. Thus, the SEDDS provides an effective delivery system for oral and parenteral delivery of hydrophobic active ingredients. SEDDS may provide improvements in the bioavailability of hydrophobic active ingredients. Methods of producing self-emulsifying dosage forms are known in the art include, but are not limited to, for example, U.S. Pat. Nos. 5,858,401, 6,667,048, and 6,960,563.

Exemplary emulsifiers are ethyl alcohol, isopropyl alcohol, ethyl carbonate, ethyl acetate, benzyl alcohol, benzyl benzoate, propylene glycol, 1,3-butyleneglycol, dimethylformamide, sodium lauryl sulfate, sodium docusate, cholesterol, cholesterol esters, taurocholic acid, phosphotidylcholine, oils, such as cottonseed oil, groundnut oil, corn germ oil, olive oil, castor oil, and sesame oil, glycerol, tetrahydrofurfuryl alcohol, polyethylene glycols, fatty acid esters of sorbitan, or mixtures of these substances, and the like.

In certain preferred embodiments, the liquid pharmaceutical formulation comprises ganaxolone, hydroxypropyl methylcellulose, polyvinyl alcohol, sodium lauryl sulfate, simethicone, methyl paraben, propyl paraben, sodium benzoate, citric acid, and sodium citrate at pH 3.8-4.2. The suspension may comprise ganaxolone at a concentration of 50 mg/ml. The formulation may further comprise a pharmaceutically acceptable sweetener (e.g., sucralose) and/or a pharmaceutically acceptable flavorant (e.g., cherry). The formulation may be enclosed, e.g., in a 120 mL, 180 mL, 240 mL, or 480 mL bottle.

A formulation for oral administration may be an oral solid dosage form (e.g., an oral capsule or tablet) or a liquid (e.g., an oral suspension comprising ganaxolone). In certain embodiments, the oral suspension is administered to the patient via the use of an oral syringe.

In certain preferred embodiments, the oral solid formulation of the present invention may be a formulation as described and prepared in Applicant's prior U.S. Pat. No. 7,858,609, entitled "Solid Ganaxolone Formulations and Methods for the Making and Use Thereof", hereby incorporated by reference in its entirety. However, the oral solid dosage formulation of ganaxolone may be prepared in accordance with other methods known to those skilled in the art.

For example, as disclosed in U.S. Pat. No. 7,858,609, the oral solid formulation may comprise stabilized particles comprising ganaxolone, a hydrophilic polymer, a wetting agent, and an effective amount of a complexing agent that stabilizes particle growth after an initial particle growth and endpoint is reached, the complexing agent being a small organic molecule having a molecular weight less than 550 and containing a moiety selected from the group consisting of a phenol moiety, an aromatic ester moiety and an aromatic acid moiety, wherein the stabilized particles have a volume weighted median diameter (D50) of the particles is from about 50 nm to about 500 nm, the complexing agent being present in an amount from about 0.05% to about 5% w/w, based on the weight particles of the solid. The hydrophilic polymer may be in an amount from about 3% to about 50%, w/w, based on the weight of the solid particles. The wetting agent may be an amount from about 0.01% to about 10%, w/w, based on the weight of the solid particles. Ganaxolone may be in an amount from about 10% to about 80% (and in certain embodiments form about 50% to about 80%) based on the weight of the stabilized particles. The stabilized particles may exhibit an increase in volume weighted median diameter (D50) of not more than about 150% when the particles are dispersed in simulated gastric fluid (SGF) or simulated intestinal fluid (SIF) at a concentration of 0.5 to 1 mg ganaxolone/mL and placed in a heated bath at 36° to 38° C. for 1 hour as compared to the D50 of the stabilized particles when the particles are dispersed in distilled water under the same conditions, wherein the volume weighted median diameter (D50) of the stabilized particles dispersed in SGF or SIF is less than about 750 nm. The stabilized particles may exhibit an increase in volume weighted median diameter (D50) of not more than about 150% when the formulation is dispersed in 15 mL of SGF or SIF at a concentration of 0.5 to 1 mg ganaxolone/mL as compared to the D50 of the stabilized particles when the particles are dispersed in distilled water under the same conditions, wherein the volume weighted median diameter (D50) of the stabilized particles dispersed in SGF or SIF is less than about 750 nm. The solid stabilized particles may be combined with optional excipients and prepared for administration in the form of a powder, or they may be incorporated into a dosage form selected from the group consisting of a tablet or capsule. The complexing agent may be a paraben, benzoic acid, phenol, sodium benzoate, methyl anthranilate, and the like. The hydrophilic polymer may be a cellulosic polymer, a vinyl polymer and mixtures thereof. The cellulosic polymer may be a cellulose ether, e.g., hydroxypropymethylcellulose. The vinyl polymer may be polyvinyl alcohol, e.g., vinyl pyrrolidone/vinyl acetate copolymer (S630). The wetting agent may be sodium lauryl sulfate, a pharmaceutically acceptable salt of docusate, and mixtures thereof. When the particles are incorporated into a solid dosage form, the solid dosage form may further comprise at least one pharmaceutically acceptable excipient, e.g., an ionic dispersion modulator, a water soluble spacer, a disintegrant, a binder, a surfactant, a plasticizer, a lubricant, a diluent and any combinations or mixtures thereof. The water soluble spacer may be a saccharide or an ammonium salt, e.g., fructose, sucrose, glucose, lactose, mannitol. The surfactant may be, e.g., polysorbate. The plasticizer may be, e.g., polyethylene glycol. The disintegrant may be cross-linked sodium carboxymethylcellulose, crospovidone, mixtures thereof, and the like.

A capsule may be prepared, e.g., by placing the bulk blend ganaxolone formulation, described herein, inside of a capsule. In some embodiments, the ganaxolone formulations (non-aqueous suspensions and solutions) are placed in a soft gelatin capsule. In other embodiments, the ganaxolone formulations are placed in standard gelatin capsules or non-gelatin capsules such as capsules comprising HPMC. In other embodiments, the ganaxolone formulations are placed in a sprinkle capsule, wherein the capsule may be swallowed whole or the capsule may be opened and the contents sprinkled on food prior to eating. In some embodiments of the present invention, the therapeutic dose is split into multiple (e.g., two, three, or four) capsules. In some embodiments, the entire dose of the ganaxolone formulation is delivered in a capsule form.

Preferably, each capsule contains about 200 to about 600 mg ganaxolone, about 300 to about 600 mg ganaxolone, about 400 to about 600 mg ganaxolone, about 500 to about 600 mg ganaxolone, about 200 mg ganaxolone, about 250 mg ganaxolone, about 300 mg ganaxolone, about 500 mg ganaxolone or about 600 mg ganaxolone. In certain embodiments, each capsule contains either 200 mg or 225 mg ganaxolone, and hydroxypropyl methylcellulose, sucrose, polyethylene glycol 3350, polyethylene glycol 400, sodium lauryl sulfate, sodium benzoate, citric acid anhydrous, sodium methyl paraben, microcrystalline cellulose, 30% Simethicone Emulsion, gelatin capsules, polysorbate 80, and sodium chloride. In some of the embodiments, the size of the capsule is 00.

Alternatively, the oral dosage forms of the present invention may be in the form of a controlled release dosage form, as described in U.S. Pat. No. 7,858,609.

In certain preferred embodiments, the oral solid formulation of the present invention may be a formulation as described and prepared U.S. Pat. No. 8,367,651.

As described in U.S. Pat. No. 8,367,651, solid stabilized particles may comprise ganaxolone, a hydrophilic polymer, a wetting agent, and an effective amount of a complexing agent that stabilizes particle growth after an initial particle growth and endpoint is reached, the complexing agent being a small organic molecule having a molecular weight less than 550 and containing a moiety selected from the group consisting of a phenol moiety, an aromatic ester moiety and an aromatic acid moiety, wherein the stabilized particles have a volume weighted median diameter (D50) of the particles is from about 50 nm to about 500 nm and the concentration of ganaxolone in the solid stabilized particles is at least 50% by weight. The hydrophilic polymer maybe in an amount from about 3% to about 50%, w/w, based on the weight of the solid particles. The wetting agent may be in an amount from about 0.01% to about 10%, w/w, based on the weight of the solid particles. In some of the embodiments, the stabilized particles exhibit an increase in volume weighted median diameter (D50) of not more than about 150% when the particles are dispersed in simulated gastric fluid (SGF) or simulated intestinal fluid (SIF) at a concentration of 0.5 to 1 mg ganaxolone/mL and placed in a heated bath at 36° to 38° C. for 1 hour as compared to the D50 of the stabilized particles when the particles are dispersed in distilled water under the same conditions, wherein the volume weighted median diameter (D50) of the stabilized particles dispersed in SGF or SIF is less than about 750 nm. In some embodiments, the stabilized particles exhibit an increase in volume weighted median diameter (D50) of not more than about 150% when the formulation is dispersed in 15 mL of SGF or SIF at a concentration of 0.5 to 1 mg ganaxolone/mL as compared to the D50 of the stabilized particles when the particles are dispersed in distilled water under the same conditions, wherein the volume weighted median diameter (D50) of the stabilized particles dispersed in SGF or SIF is less than about 750 nm. In some embodiments, ganaxolone may be present in an amount greater than 50% to about 80%, based on the weight of the particles. In some embodiments, the stabilized particles may exhibit an increase in volume weighted median diameter (D50) of not more than about 150% when the particles are dispersed in simulated gastric fluid (SGF) or simulated intestinal fluid (SIF) at a concentration of 0.5 to 1 mg ganaxolone/mL and placed in a heated bath at 36° to 38° C. for 1 hour, as compared to the D50 of the stabilized particles when the particles are dispersed in distilled water under the same conditions, wherein the volume weighted median diameter (D50) of the stabilized particles dispersed in SGF or SIF is less than about 750 nm. In some embodiments, the solid stabilized particles may be in the form of a powder. In some embodiments, the particles may be incorporated into a dosage form selected from the group consisting of a tablet or capsule. In some embodiments, the volume weighted median diameter (D50) of the stabilized particles dispersed in distilled water is from about 100 nm to about 350 nm. In some embodiments, the complexing agent is selected from the group consisting of parabens, benzoic acid, methyl anthranilate, and pharmaceutically acceptable salts thereof and mixtures thereof. In some embodiments, paraben is selected from the group consisting of methylparaben, ethylparaben, propylparaben, pharmaceutically acceptable salts thereof and mixtures thereof. In some embodiments, the hydrophilic polymer is selected from the group consisting of a cellulosic polymer, a vinyl polymer and mixtures thereof.

In some embodiments, the cellulosic polymer is a cellulose ether. In some embodiments, the cellulose ether is hydroxypropylmethylcellulose. In some embodiments, the vinyl polymer is polyvinyl alcohol. In some embodiments, the wetting agent is selected from the group consisting of sodium lauryl sulfate, a pharmaceutically acceptable salt of docusate, and mixtures thereof. Is some embodiments, the particles are incorporated into a solid dosage form, further comprising at least one pharmaceutically acceptable excipient selected from the group consisting of an ionic dispersion modulator, a water soluble spacer, a disintegrant, a binder, a surfactant, a plasticizer, a lubricant, and any combinations or mixtures thereof. In some embodiments, the pharmaceutically acceptable excipient comprises an ionic dispersion modulator. In some embodiments, the ionic dispersion modulator is in an amount from about 1% to about 50%, w/w, based on the weight of the solid particles. In some embodiments, the ionic dispersion modulator is a salt. In some embodiments, the ionic dispersion modulator is an inorganic salt is selected from the group consisting of a magnesium salt, a calcium salt, a lithium salt, a potassium salt, a sodium salt and mixtures thereof. In some embodiments, the ionic dispersion modulator is an organic salt is selected from the group consisting of a citrate salt, a succinate salt, a fumarate salt, a malate salt, maleate salt, a tartrate salt, a glutarate salt, a lactate salt and mixtures thereof. In some embodiments, the pharmaceutically acceptable excipient comprises a water soluble spacer. In some embodiments, the water soluble spacer is in an amount from about 2% to about 60%, w/w, based on the weight of the solid particles. In some embodiments, the water soluble spacer is a saccharide or an ammonium salt. In some embodiments, the saccharide is selected from the group consisting of fructose, sucrose, glucose, lactose, mannitol and mixtures thereof. In some embodiments, the disintegrant is selected from the group consisting of cross-linked sodium carboxymethylcellulose, crospovidone and any combinations or mixtures thereof. In some embodiments, the surfactant is a polysorbate. In some embodiments, the plasticizer is polyethylene glycol. In some embodiments, the solid dosage form is an immediate release dosage form. In some embodiments, the solid dosage form is a controlled release dosage form. In some embodiments, the particles are incorporated into an oral solid dosage form comprising (i) a controlled release component comprising a first portion of the stabilized particles; and a controlled release material, and (ii) an immediate release component comprising a second portion of the stabilized particles, the first and second portion of stabilized particles having a volume weighted median diameter (D50) of from about 50 nm to about 500 nm. In some embodiments, the ratio of ganaxolone in controlled release to immediate release is from about 4:1 to about 1:4. In some embodiments, the dosage form provides a therapeutic effect for about 8 to about 24 hours after administration. In some embodiments, the complexing agent is in an amount from about 0.05% to about 5%, w/w, based on the weight of the solid particles. In some embodiments, the complexing agent comprises methylparaben or a salt thereof. In some embodiments, the complexing agent comprises benzoic acid or a salt thereof. In some embodiments, the complexing agent comprises methyl anthranilate. In some embodiments, the formulation includes from about 200 mg to about 800 mg ganaxolone.

As further described in U.S. Pat. No. 8,367,651, solid stabilized particles may also comprise ganaxolone, a hydrophilic polymer, a wetting agent, and an effective amount of a complexing agent selected from the group of small organic molecules having a molecular weight less than 550 and containing a moiety selected from the group consisting of a phenol moiety, an aromatic ester moiety and an aromatic acid moiety, the stabilized particles having a volume weighted median diameter (D50) of the particles from about 50 nm to about 500 nm, the concentration of ganaxolone in the solid stabilized particles being at least 50% by weight. In some embodiments, ganaxolone is present in an amount greater than 50% to about 80%, based on the weight of the particles. In some embodiments, the particles are incorporated into a dosage form selected from the group consisting of a tablet or capsule. In some embodiments, the complexing agent is selected from the group consisting of parabens, benzoic acid, methyl anthranilate, and pharmaceutically acceptable salts thereof and mixtures thereof.

In certain preferred embodiments, the formulation of the present invention may be a pharmaceutical composition described in U.S. Pat. No. 9,029,355.

In certain embodiments, the composition may comprise the ganaxolone nanoparticles as described above, further in formulations as described in U.S. Pat. No. 9,029,355. In some embodiments, the pharmaceutical composition is a compressed tablet. In some embodiments, the pharmaceutical composition is contained inside a capsule.

The formulation can be an intravenous formulation of ganaxolone. The intravenous formulation of ganaxolone can comprise a cyclodextrin (e.g., a sulfobutyl ether O-cyclodextrin (CAPTISOL®). The IV solution can comprise a sterile ready to administer solution containing 1 mg/ml ganaxolone in CAPTISOL® (CAPTISOL®: GNX ratio 60:1). The ready to administer solution can comprise 1 mg/ml ganaxolone in sulfobutyl ether O-cyclodextrin (CAPTISOL®) having a Captisol to ganaxolone ratio of 60:1, and a buffer (i.e., phosphate and/or sodium chloride). In embodiments, the IV solution is a sterile solution containing 3 mg/ml ganaxolone in CAPTISOL® (Sulfobutylether-β-Cyclodextrin) (CAPTISOL®: GNX ratio 70:1) or 5 mg/ml ganaxolone in Captisol, each of which may or may not be may be diluted with 0.9% saline (i.e., sodium chloride) solution, for example to produce a 1 mg/ml ganaxolone solution for administration, prior to administration.

In certain embodiments, the formulation (e.g., an intravenous formulation) comprises ganaxolone and sulfobutylether-β-cyclodextrin (e.g., CAPTISOL®) in a weight ratio from about 1:50 to about 1:75. In some of these embodiments, the weight ratio ganaxolone and Captisol® is about 1:51, about 1:52, about 1:53, about 54:1, about 1:55, about 1:56, about 1:57, about 1:58, about 1:59, about 1:60, about 1:61, about 1:62, about 1:63, about 1:64, about 1:65, about 1:66, about 1:67, about 1:68, about 1:69, about 1:70, about 1:71, or about 1:72. In some of these embodiments, the weight ratio ganaxolone and CAPTISOL® is about 1:60.

The intravenous formulation may be selected, e.g., from the group consisting of nanocrystal formulations; emulsions; lyocells; solvents or surfactants; liposomes; microemulsions; and liquids containing solid-lipid nanoparticles.

In certain embodiments, the intravenous formulation is an IV solution. An intravenous formulation is preferably a sterile liquid (e.g., aqueous liquid in the form of an emulsion, a suspension, a solution and the likes). In some of these embodiments, the IV solution comprises ganaxolone and a pharmaceutically acceptable solvent(s) and/or oil(s) that can solubilize ganaxolone.

In certain embodiments, the intravenous formulation is an oil-in-water emulsion.

In certain embodiments, the intravenous formulation is a liquid nanoparticulate formulation (e.g., a liquid comprising nanoparticles of ganaxolone). In some of the embodiments, the nanoparticulate formulation comprises ganaxolone and a polymeric and/or ionic stabilizer and is free from complexing agents. In certain embodiments, the polymeric and ionic stabilizers are selected from the group consisting of surfactants. In certain embodiments, surfactants are selected from the group consisting of sorbitan esters, polyoxyethylene sorbitan fatty acid esters, poloxamers, cholesterol salts, and bile salts.

In certain embodiments, the formulation for the intravenous infusion may be a formulation as described and prepared in U.S. Patent Publication No. 2017/0258812 or U.S. Patent Publication No. 2016/0228454. However, formulations for the intravenous infusion may be prepared in accordance with other methods known to those skilled in the art.

As described in U.S. Patent Publication No. 2016/0228454, an aqueous injectable ganaxolone formulation may comprise a) ganaxolone and sulfobutyl ether-β-cyclodextrin in an inclusion complex; and b) water. In some embodiments, the complex comprising ganaxolone and sulfobutyl ether-β-cyclodextrin comprises a 1:1 ganaxolone:sulfobutyl ether-β-cyclodextrin complex; and the w/w ratio of sulfobutyl ether-β-cyclodextrin to ganaxolone is about 52:1 or greater. In some embodiments, the formulation may further comprise surfactant. In some embodiments, the surfactant is a sorbitan ester, a polyoxyethylene sorbitan fatty acid ester, a poloxamer, a cholesterol salt, or a bile salt. In some embodiments, the surfactant may comprise from about 1 to about 15 percent of the formulation by weight. In some embodiments, the surfactant is polysorbate 80. In some embodiments, the formulation further comprises a buffer and has a pH of about 6.0 to about 7.6. In some embodiments, the buffer is a phosphate buffer. In some embodiments, the buffer is a combination of a monobasic phosphate buffer and a dibasic phosphate buffer, wherein the concentration of each phosphate buffer is 2 mM to 50 mM. In some embodiments, the buffer is a phosphate buffer. In some embodiments, the buffer is a combination of a monobasic phosphate buffer and a dibasic phosphate buffer, wherein the concentration of each phosphate buffer is 2 mM to 50 mM. In some embodiments, the concentration of ganaxolone is 2 mg/ml to 8 mg/ml, the w/w ratio of sulfobutyl ether-β-cyclodextrin to ganaxolone is within the range from about 52:1 to about 90:1; the formulation contains a buffer and has a pH of 6.7 to 7.3 or a pH of 6.0 to 7.0; and the formulation contains from 1 to 15 weight percent surfactant. In some embodiments, the concentration of ganaxolone is 1 mg/ml to 5 mg/ml; the weight percent of sulfobutyl ether-β-cyclodextrin 25% to 35%; and the formulation contains from 5% to 15% (weight percent) of at least one of the following: a surfactant, ethanol, glycerin, or propylene glycol. In some embodiments, the formulation further comprises a preservative. In some embodiments, the preservative is benzyl alcohol, chlorbutanol, 2-ethoxyethanol, parabens (including methyl, ethyl, propyl, butyl, and combinations), benzoic acid, sorbic acid, chlorhexidene, phenol, 3-cresol, thimerosal, or a phenylmercurate salt.

As further described in U.S. Patent Publication No. 2016/0228454, the formulation may be a lyophilized ganaxolone formulation comprising ganaxolone and sulfobutyl ether-β-cyclodextrin, wherein the ganaxolone formulation is 1.0% to 1.5% ganaxolone. In some embodiments, the formulation may further comprise a bulking agent. In some embodiments, the bulking agent is mannitol, lactose, sucrose, trehalose, sorbitol, glucose, rafinose, glycine, histidine, polyethylene glycol (PEG), or polyvinyl pyrrolidone (PVP).

Ganaxolone formulations suitable for parenteral administration in the methods of the present invention may comprise physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents, or vehicles including water, ethanol, polyols (propylene glycol, polyethyleneglycol, glycerol, cremophor and the like), suitable mixtures thereof, vegetable oils (such as olive oil) and injectable organic esters such as ethyl oleate. Additionally, ganaxolone can be dissolved at concentrations of >1 mg/ml using water soluble beta cyclodextrins (e.g. beta-sulfobutyl-cyclodextrin and 2-hydroxypropylbetacyclodextrin). A particularly suitable cyclodextrin is a substituted-β-cyclodextrin is CAPTISOL®. Proper fluidity can be maintained, for example, by the use of a coating such as lecithin, by the maintenance of the required particle size in the case of dispersions, and by the use of surfactants. Ganaxolone formulations suitable for subcutaneous injection may also contain additives such as preserving, wetting, emulsifying, and dispensing agents. Prevention of the growth of microorganisms can be ensured by various antibacterial and antifungal agents, such as parabens, benzoic acid, benzyl alcohol, chlorobutanol, phenol, sorbic acid, and the like. It may also be desirable to include isotonic agents, such as sugars, sodium chloride, and the like. Prolonged drug absorption of the injectable pharmaceutical form can be brought about by the use of agents delaying absorption, such as aluminum monostearate and gelatin. Ganaxolone suspension formulations designed for extended release via subcutaneous or intramuscular injection can avoid first pass metabolism and lower dosages of ganaxolone will be necessary to maintain plasma levels of about 50 ng/ml. In such formulations, the particle size of the ganaxolone particles and the range of the particle sizes of the ganaxolone particles can be used to control the release of the drug by controlling the rate of dissolution in fat or muscle.

In certain embodiments, the intravenous formulation is a solution comprising a complexing agent(s). In some of these embodiments, a complexing agent is a molecule with a lipophilic core and hydrophilic outer shell capable of solubilizing ganaxolone In certain embodiments, the formulation is an IV solution comprising ganaxolone and sulfobutylether cyclodextrin (CAPTISOL®), wherein ganaxolone is solubilized in sulfobutylether cyclodextrin (CAPTISOL®). In some embodiments, the solution comprises 3 mg of ganaxolone per 1 ml of the solution and is sterile. In certain embodiments, the solution is stable for at least 18 months, is stored refrigerated at a temperature from about 4° C. to about 8° C.

E. Definitions

Various terms relating to aspects of the description are used throughout the specification and claims. Such terms are to be given their ordinary meaning in the art unless otherwise indicated. Other specifically defined terms are to be construed in a manner consistent with the definitions provided herein.

The abbreviation "EEG" means electroencephalography.

The terms "subject" and "patient" are used interchangeably herein to refer to any animal, such as any mamma, including but not limited to, humans, non-human primates, rodents, and the like. The mammal is preferably a human.

The term "effective amount" or "therapeutically effective amount" as used herein refers to an amount of a compound described herein (e.g., ganaxolone) that is sufficient to effect the intended result, including, but not limited to disease treatment as illustrated below. The "therapeutically effective amount" can be an amount effective to manage seizure activity, suppress seizure, allow the patient to recover from a hyperexcitable state, prevents seizure-relapse, or can provide continued suppression of seizure. The therapeutically effective amount can vary depending upon the intended application, or the subject and the disease condition being treated, e.g., the weight and age of the subject, the severity of the disease condition, the manner of administration and the like.

The term "pharmaceutical compositions" as used herein are compositions comprising at least one active agent, such as a compound or salt, solvate, or hydrate of ganaxolone, and at least one other substance, such as a carrier. Pharmaceutical compositions optionally contain one or more additional active agents. When specified, pharmaceutical compositions meet the U.S. FDA's GMP (good manufacturing practice) standards for human or non-human drugs. "Pharmaceutical combinations" are combinations of at least two active agents which may be combined in a single dosage form or provided together in separate dosage forms with instructions that the active agents are to be used together to treat a disorder, such as status epilepticus.

As used herein, the terms "treat," "treatment," or "treating" and grammatically related terms, refer to an improvement of any sign, symptoms, or consequence of the disease, such as prolonged survival, less morbidity, and/or a lessening of side effects.

5. EQUIVALENTS

It will be readily apparent to those skilled in the art that other suitable modifications and adaptions of the methods of the invention described herein are obvious and may be made using suitable equivalents without departing from the scope of the disclosure or the embodiments. Having now described certain compounds and methods in detail, the same will be more clearly understood by reference to the following examples, which are introduced for illustration only and not intended to be limiting.

6. EXAMPLES

Example 1. Phase 2 Open-Label Clinical Trial for TSC

A Phase 2 open-label 12 week trial of adjunctive ganaxolone treatment (Part A) in tuberous sclerosis complex-related epilepsy followed by long-term treatment (Part B) was conducted. This was a multicenter study conducted at 7 sites in the United States.

The primary objectives were to assess preliminary safety and efficacy of ganaxolone (GNX) as adjunctive therapy for the treatment of primary seizure types in patients with genetically- or clinically-confirmed TSC-related epilepsy through the end of the 12 week treatment period. The primary seizure types (focal motor seizures without impairment of consciousness or awareness, focal seizures with impairment of consciousness or awareness, focal seizures evolving to bilateral, tonic-clonic convulsive seizures, and generalized motor seizures including tonic-clonic, bilateral tonic, bilateral clonic, or atonic/drop seizures) are identified to be the most common, easily identifiable/countable by a parent/caregiver/legally authorized representative (LAR), and most consequential to the patient's quality of life.

Secondary Objectives were 1) to assess the long-term efficacy of GNX when administered as adjunctive therapy throughout the open label extension (OLE) period (Part B); and 2) to assess the long-term safety and tolerability of GNX when administered as adjunctive therapy throughout the OLE period (Part B)

Methodology

This was an open label (OL) proof of concept study of adjunctive GNX treatment in patients with a confirmed clinical diagnosis of TSC and/or a mutation in either the TSC1 or TSC2 gene. The trial consisted of two parts: Part A consisted of a 4-week baseline period followed by a 12-week treatment period (4-week titration and 8-week maintenance). For patients not continuing in the OLE period (Part B), a 2-week taper period followed by a 2-week safety period followed. The main difference between Part A and Part B is the length of treatment, less frequent assessments, and the ability to alter drug doses (both GNX and other antiepileptic drug [AED] treatments which includes initiating and stopping other medications) based on investigator evaluation of the patient's clinical course during Part B. Patients with a seizure frequency reduction rate of ≥35% during the 12-week treatment period in Part A compared to baseline were eligible to continue into Part B ("OLE eligible").

Part A 4-week baseline period
4-week titration period
8-week maintenance period
2-week taper period (For patients who did not complete Part A or after completing Part A but did not continue into Part B)
2-week safety follow-up visit post taper (For patients who tapered off GNX)

Part B (Optional for OLE-Eligible Patients)

OLE period (until the Sponsor markets ganaxolone or terminates the study)
2-week taper period (For patients who discontinued GNX due to early termination or completion)
2-week safety follow-up visit post taper (For patients who tapered off GNX)

Part A included a 4-week baseline and 4 weeks of investigational product (IP) titration followed by 8 weeks of dose maintenance followed by 2-week taper for those patients that did not continue into the Part B OLE period. After meeting all eligibility criteria, approximately 30 patients aged 2 to 65 years (inclusive) with TSC-related epilepsy were enrolled to receive GNX for a total of 12 weeks (4 week titration, 8 week maintenance) in addition to their standard anti-seizure medication(s) (ASMs). Patients were titrated to 63 mg/kg/day (maximum 1800 mg/day) over 4 weeks, and then maintained at that dose for another 8 weeks. Patients who were not able to tolerate 63 mg/kg/day (or maximum 1800 mg/day) were eligible to be maintained on a lower dose after discussion with the medical monitor. A minimum dose of 33 mg/kg/day or 900 mg/day was generally required during the maintenance period.

For Part A, dose changes including alternative dosing paradigm (e.g., lower dose during the daytime and higher dose in the evening) were to be discussed with the sponsor medical monitor prior to making the change or within 48 hours of making the change. Patients who discontinue GNX were advised to undergo a 2-week taper period, unless otherwise medically indicated. Patients who discontinue GNX before the completion of the maintenance period were followed per protocol and, at a minimum, patients were encouraged to maintain daily seizure diaries until the maintenance period in Part A was completed. These patients also returned to the site 2 weeks after the taper for safety follow-up assessments.

After completing the initial 16-week period, Part A, patients with a seizure reduction of ≥35% compared to the 4-week baseline period and who did not have any other contraindications for continued treatment we eligible continue to be treated with GNX in the OLE period (Part B).

Patients were required to complete a daily diary to determine GNX's effect on seizures. Days without seizures should also have been noted. Additional clinician and caregiver administered instruments were used to assess the efficacy of GNX in TSC and included: Caregiver Global Impression of Change (CGI-C)-Target Behavior and Clinical Global Impression-Improvement (CGI-I) caregiver and CGI-I clinician. Pharmacokinetics, Safety and tolerability were assessed.

Investigational Product, Dose, and Mode of Administration

Ganaxolone was administered in increments of 15 mg/kg/day up to 63 mg/kg/day (maximum 1800 mg/day) given as an oral suspension with food. Patients weighing≤28 kg were dosed on an mg/kg basis. Patients weighing>28 kg were dosed on a fixed regimen in increments of 450 mg/day up to 1800 mg/day. Ganaxolone was administered during the 4-week titration period as shown in Table 1.

TABLE 1

Oral Suspension Dosing[a] for Patients Weighing ≤28 kg (62 lbs)[b]

| Dose mg/kg | Total mg/kg/day | Days |
|---|---|---|
| 6 TID | 18 | 1-7 |
| 11 TID | 33 | 8-14 |
| 16 TID | 48 | 15-21 |
| 21 TID | 63 | 22-28 |

Oral Suspension Dosing[a] for Patients Weighing >28 kg (62 lbs)[c]

| Dose mg | mL per Dose | Total mg/day | Days |
|---|---|---|---|
| 150 TID | 3 | 450 | 1-7 |
| 300 TID | 6 | 900 | 8-14 |
| 450 TID | 9 | 1350 | 15-21 |
| 600 TID | 12 | 1800 | 22-28 |

TID = 3 times daily.
[a]administered in 3 divided doses following a meal or snack.
[b]Patients weighing ≤28 kg were dosed according to the patient's weight in kilograms.
[c]Patients weighing >28 kg were dosed on a fixed regimen in increments of 450 mg/day up to 1800 mg/day.

Any patient that did not tolerate the next dose step could be maintained at the lower dose step for additional days before advancing to the next dose. If the next dose was still not tolerated, the patient could drop back to the next lower dose step. A minimum dose of 33 mg/kg/day or 900 mg/day was generally required following the escalation period, during the maintenance period.

Criteria for Evaluation

Seizures: All seizure types and number of seizures were to be recorded daily in a diary. Days in which no seizures occur were also to be noted.

Primary Efficacy Endpoint: The primary efficacy endpoint was the percent change in 28-day primary seizure frequency through the end of the 12-week treatment period (4-week titration and 8-week maintenance) relative to the 4-week baseline. The primary seizure types were defined as the following: focal motor seizures without impairment of consciousness or awareness, focal seizures with impairment of consciousness or awareness, focal seizures evolving to bilateral, tonic-clonic seizures, and generalized motor seizures including tonic-clonic, bilateral tonic, bilateral clonic, and atonic/drop seizures.

Secondary Efficacy Endpoints (Seizure control): Derived seizure secondary efficacy endpoints was based on data through the end of the 12-week treatment period relative to the 4-week prospective baseline period. Percentage of patients experiencing a ≥50% reduction in 28-day primary seizure frequency through the end of the 12-week treatment period compared to the 4-week Baseline Period.

Results

Approximately 24 tuberous sclerosis complex (TSC) patients were screened to achieve 23 TSC patients enrolled in Part A. 17 patients (73.9%) completed Part A and 6 patients (26.1%) discontinued Part A. Of the patients that discontinued Part A, 4 discontinued because of an adverse event, one discontinued because of a lack of efficacy and one withdrew consent. The enrolled patients were patients were receiving the concomitant antiepileptic drugs (AED) as shown in Table 2.

TABLE 2

| Concomitant AED | Number of patients (%) |
| --- | --- |
| Cannabidiol | 12 (52.2) |
| Everolimus | 11 (47.8) |
| Vigabatrin | 8 (34.8) |
| lacosamide | 7 (30.4) |

Figure 1:
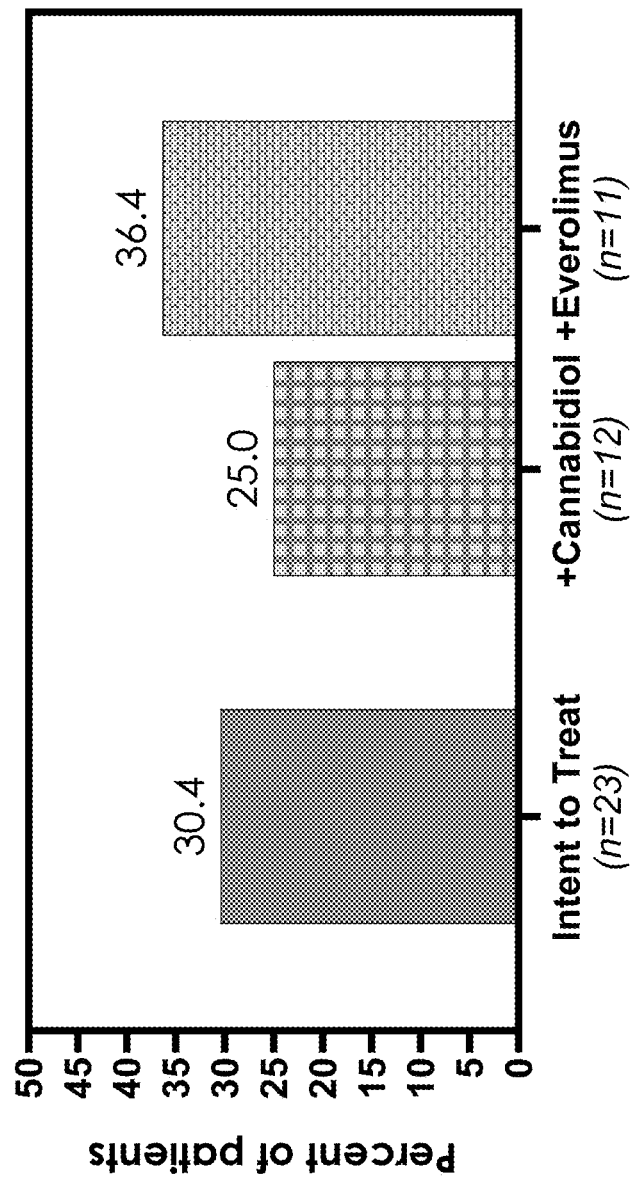

There was a 16.6% (median) reduction in TSC-associated seizure frequency in the 23 enrolled patients. 30.4% of the enrolled patients (n=23), but only 25% of patients that received concomitant cannabidiol (n=12), and 36.4% of patients that received concomitant everolimus (n=11) achieved≥50% reduction in TSC-associated seizure frequency. FIG. 1

Figure 2:
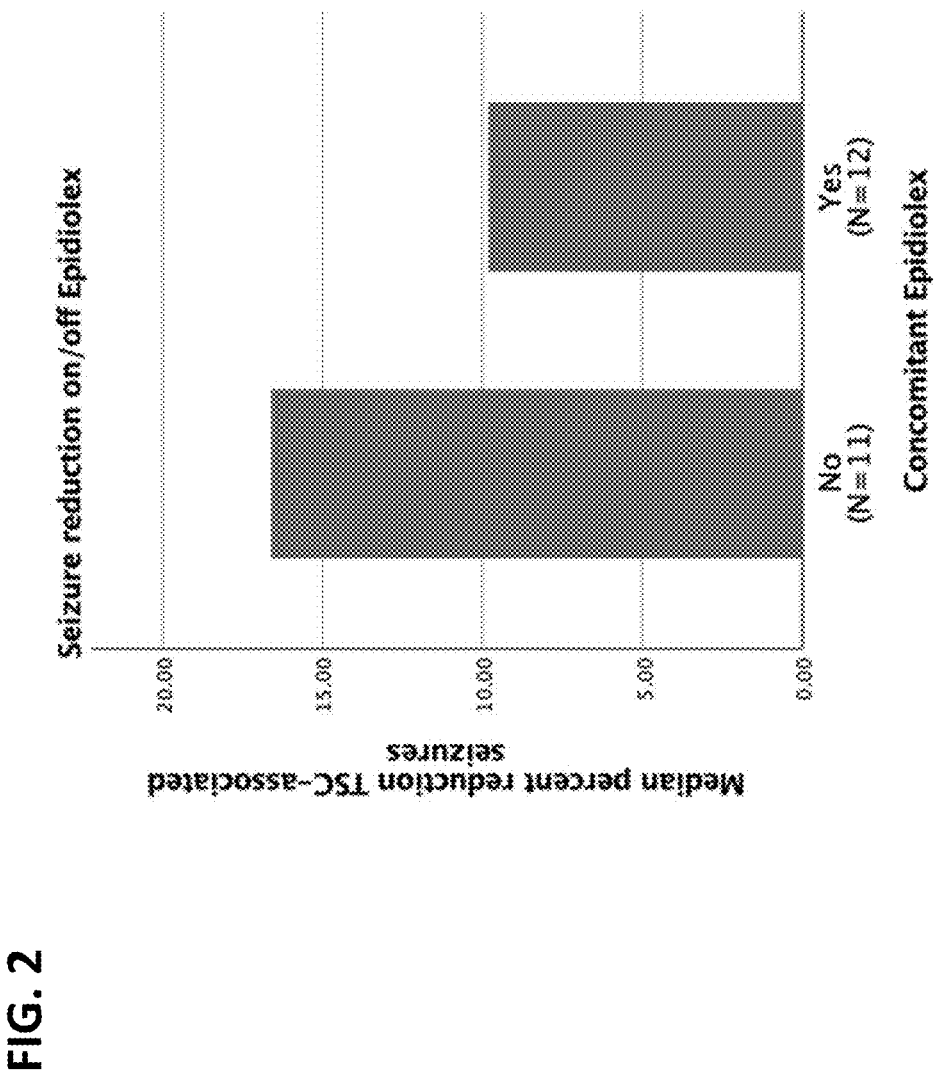
FIG. 2 is a graph depicting the median percent reduction of TSC-related seizures in a clinical trial of ganaxolone. Subjects who were not receiving concomitant EPIDIOLEX (CBD) had a greater reduction in seizure (left column) than those subjects who received concomitant EPIDIOLEX (CBD) (right column).

There was a greater median percent reduction in TSC-associated seizures in patients that did not receive concomitant cannabidiol (n=11) in comparison to patient that received cannabidiol. FIG. 2

Focal seizure types accounted for >80% of all TSC-associated seizures, and there was a median percent reduction in focal seizure frequencies of 25.2% (n=19).

Ganaxolone was generally well-tolerated, with somnolence reported as the most common adverse event (reported in 10 patients (43.5%)). Sedation was reported in 3 patients (13.0%), and fatigue was reported in 3 patients (13.0%). One patient experienced seizure that was assessed by the principal investigator as treatment related.

Figure 3:
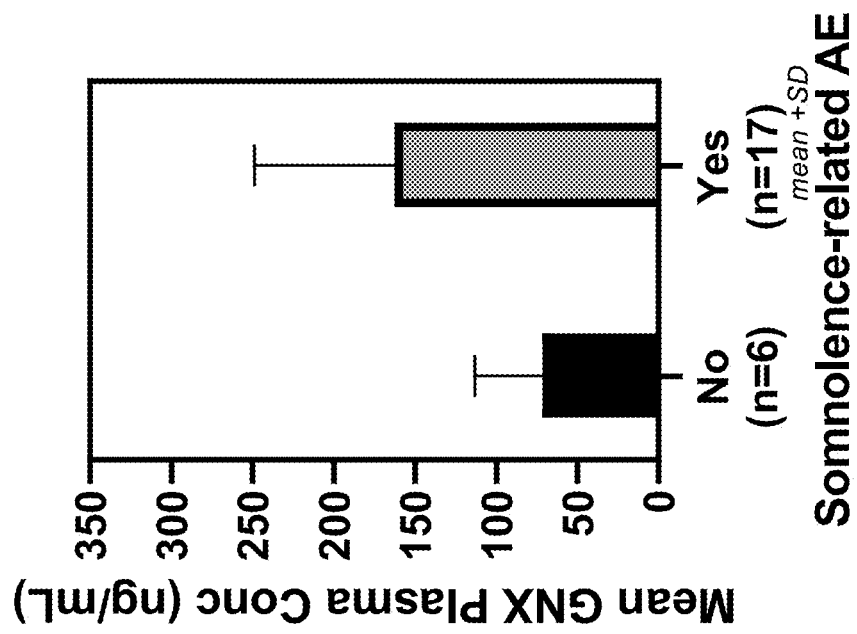
FIG. 3 is a graph depicting showing the relationship between Ganaxolone plasma concentration and somnolence-related adverse events. Somnolence-related adverse events were more prevalent in patients with a higher ganaxolone plasma concentration.

Somnolence-related adverse events (includes somnolence, sedation, fatigue and lethargy) occurred in 17 patients. Patients that reported these adverse events had a higher mean ganaxolone serum concentration relative to patients that did not report such adverse events. FIG. 3

All patients receiving concomitant cannabidiol (n=12) experienced somnolence-related adverse events, and 12 of 17 patients that reported somnolence-related adverse events were receiving EPIDIOLEZ (cannabidiol).

Figure 4:
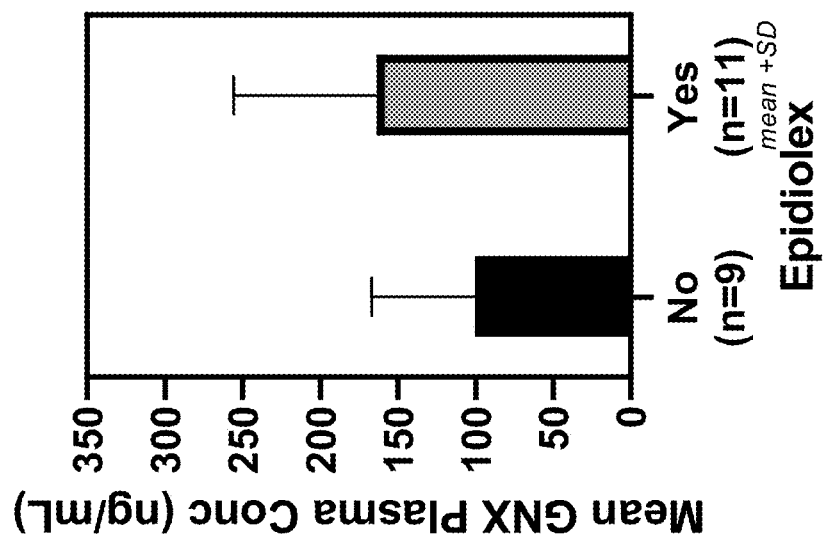
FIG. 4 is a graph showing that patients who received concomitant EPIDIOLEX (CBD) had a mean ganaxolone plasma concentration that was higher than the mean plasma concentration in patients who did not receive EPIDIOLEX (CBD). All patients receiving EPIDIOLEX (CBD) experienced somnolence-related adverse events and 12/17 patients with somnolence-related adverse events were receiving EPIDIOLEX (CBD).

Patients who received concomitant cannabidiol had higher mean ganaxolone plasma concentrations in comparison to patients that did not receiving cannabidiol. FIG. 4 The data in FIG. 4 is for an n of 23, as pK values were not available for some study subjects.

Figure 5:
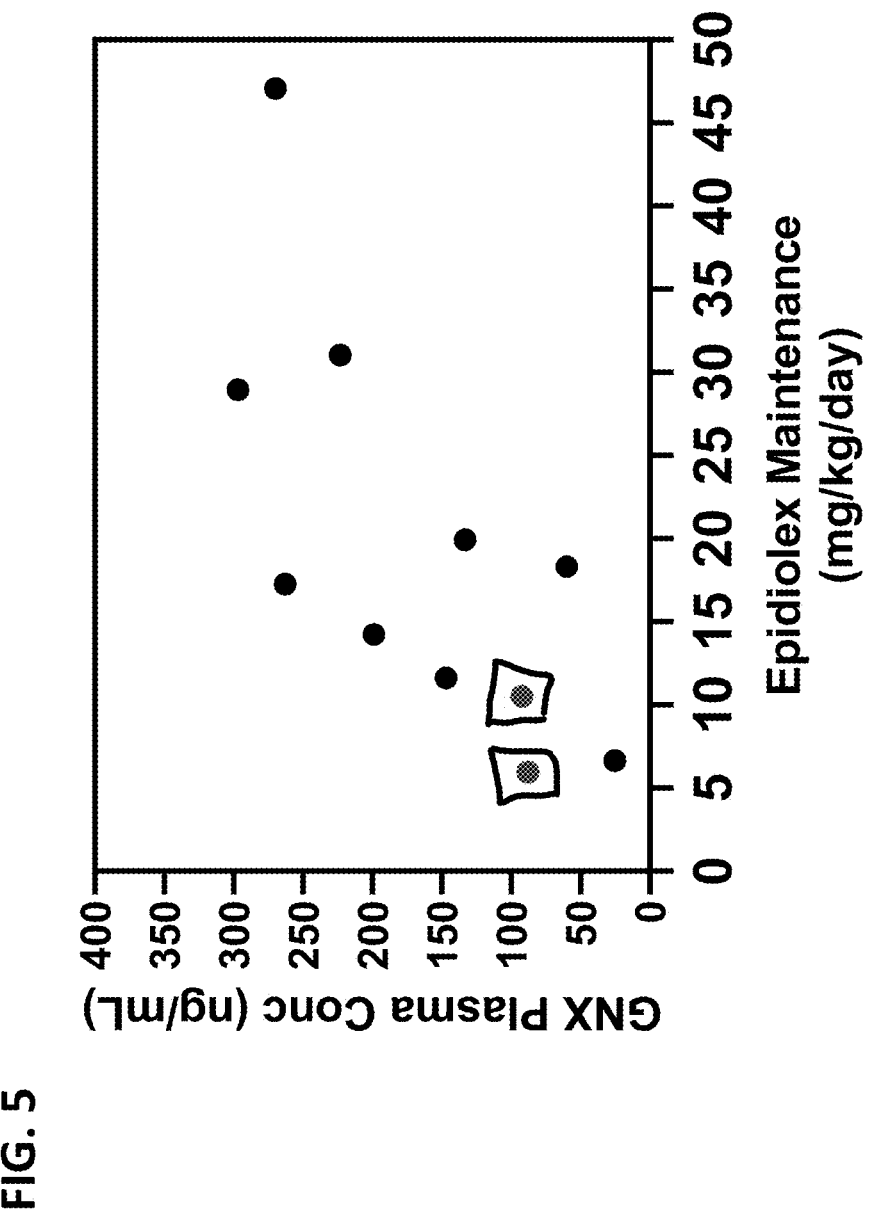
FIG. 5 is a plot showing the dosing effect concomitant EPIDIOLEX (CBD) on ganaxolone plasma concentration (ng/ml). The two boxed datapoints are patients who responded to ganaxolone treatment.
Figure 6:
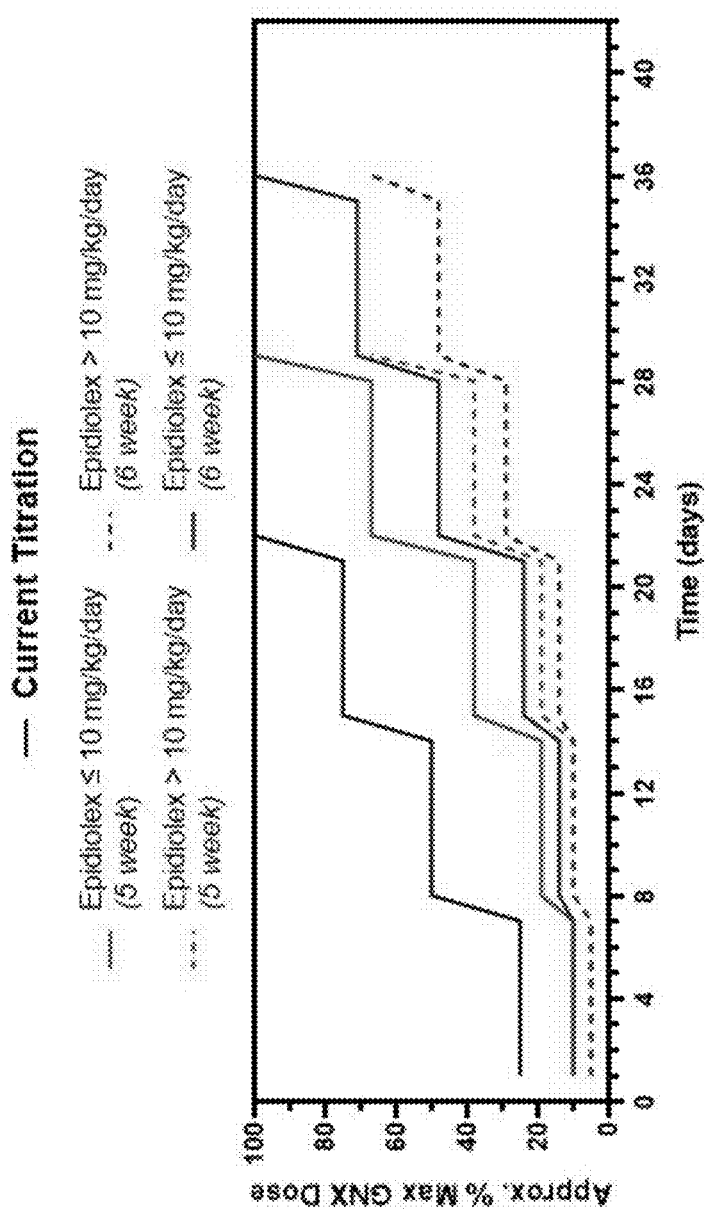
FIG. 6 is a graph depicting ganaxolone titration schedules for patients receiving concomitant EPIDIOLEX (CBD). The "current titration" is the ganaxolone titration used in the phase 2 clinical study, and the other titrations reflect adjustments based on the discovered drug interaction of ganaxolone and CBD.

The ganaxolone plasma concentration in patients receiving concomitant cannabidiol was related to the cannabidiol dose, and higher doses of cannabidiol were associated with higher plasma concentrations of ganaxolone. FIG. 5. The data in FIG. 5 are for n=1 las pK data was not available on patient who discontinued the study at week 4. The data in FIG. 5 include plasma GNX concentrations for two patients who responded to GNX treatment. (Boxed datapoints) These two patients received concomitant EPIDIOLEX (CBD) at 10 mg/kg/day or less. This dosing of concomitant EPIDOPEX was not associated with elevated ganaxolone plasma concentrations and somnolence-related adverse events, and ganaxolone showed robust efficacy in these patients (receiving concomitant EPIDOLEX (CBD) at 10 mg/kg/day or less).

Discussion of Study Results

The study enrolled a highly refractory patient population that was receiving therapy with multiple AEDs including cannabidiol and everolimus. Approximately, ⅓ of patents had a robust reduction in TSC-associated seizures, including those on concomitant cannabidiol and everolimus.

The results of the Part A surprisingly show that patients who were concomitantly treated with CBD showed lower suppression of seizure (efficacy) and experienced greater ganaxolone tolerability issues, in comparison to TSC patients who were not receiving concomitant CBD. This result correlated with a higher blood concentration of ganaxolone in patients who were also receiving CBD in comparison to patients who were not receiving CBD. These results appear to be related to a previously unknown and unexpected drug interaction between ganaxolone and CBD. This is unexpected because ganaxolone is a metabolized by CYP3A4/5. Landmark et al. Epilepsia 2021 62:857-873. Ganaxolone is not significantly metabolized by the enzymes that are implicated in CBD interactions with other drugs: UGT1A9, UGT2B7, CYP1A2, CYP2B6, CYP2C8, CYP2C9 or CYP2C19. Accordingly, it was unexpected that ganaxolone tolerability and efficacy would be adversely affected by concomitant CBD.

Example 2. Phase 3 Ganaxolone Titration Study in TSC Patients

To mitigate the observed ganaxolone drug interactions with concomitant cannabidiol, a two phase titration of ganaxolone will be used in a phase 3 clinical trial of ganaxolone in TSC. The titration schedule uses a lower ganaxolone starting dose than was used in the study described in Example 1, and will include a more gradual increase in the amount of ganaxolone that is administered until the daily dose that correlates with the absorption limit determined from population pharmacokinetic modeling in pediatric patients is achieved. At that point, the amount of ganaxolone that is administered can be increased in larger increments until the target dose is achieved (42 mg/kg/day or 1200 mg/day in patients receiving concomitant EPIDIOLEX (CBD) at 10 mg/kg/day or greater; or 63 mg/kg/day or 1800 mg/day in patient receiving concomitant EPIDI- OLEX (CBD) at less than 10 mg/kg/day) or not receiving concomitant EPIDIOLEX (CBD). See, FIGS. 6 through 9. This titration will allow the patients to become tolerized to side effects, including those that appear to have been exacerbated by concomitant cannabidiol in the phase 2 study described in Example 1, without a loss of efficacy. The maximum dose for all patients will be 1800 mg per day. Patients receiving cannabidiol who reach the target dose of ganaxolone may increase the dose of ganaxolone further based on tolerability and need for additional seizure control to a maximum of 1800 mg per day.

A Phase 3, global, double-blind, randomized, placebo-controlled study of adjunctive GNX treatment in children and adults with TSC-related epilepsy will be conducted. The study will consist of a 4-week prospective baseline phase, defined as the first 28 days following screening, followed by a double-blind phase consisting of a 4-week titration period (with 2 additional weeks allowed, if necessary, for tolerance) and a 12-week maintenance period.

Participants eligible for inclusion in this double-blind study must have inadequately controlled seizures after exposure to at least 2 AEDs administered at adequate doses and for adequate durations, with at least 8 seizures per month (approximately) in the 2 months prior to screening and seizure-free periods of not more than 1 week.

Procedures specific to this protocol and not otherwise considered standard of care, will not be performed until written informed consent from the participant or their parent/LAR, as appropriate, has been appropriately obtained.

An interactive response technology system will be used to randomize participants, dispense drug, track treatment, and maintain the blind throughout the duration of the study.

Participants or their parent/caregiver are expected to complete eDiary entries to document the number and type(s) of seizures daily throughout the study. A variety of clinician and caregiver administered instruments will be used to assess efficacy, and will include
CGI-S(Clinical Global Impression—Severity)
CGI-I (Clinical Global Impression of Improvement) by parent/caregiver and clinician
CGI-CSID (Caregiver Global Impression of Change in Seizure Intensity/Duration)
CSHQ (Caregiver Global Impression of Change in Seizure Intensity/Duration) for children or adolescents or SQS for adults
ADAMS (Anxiety, Depression, and Mood Scale)
Peds-QL-FIM (Pediatric Quality of Life—Family Impact Module)
SF-36 (Short Form 36)
ELDQOL (Epilepsy and Learning Disabilities Quality of Life)
The titration schedule is as follows:
Start—Day 1
Titration 1—Day 7
Titration 2—Day 14
Titration 3—Day 21
Final titration—Day 28
Maintenance begins on Day 29 (Start of Week 5)
GNX (or matching volumes of placebo suspension) will be titrated at approximately weekly intervals over 4 weeks to a maximum dose based on the participant's starting weight of 63 mg/kg/day with a maximum daily dose of 1800 mg (for patients>28 kg).

The participant may have the dose of IP temporarily or permanently decreased at any point in the maintenance period to manage tolerability. The maximum dose for all participants will be 1800 mg/day. The total double-blind phase (titration and maintenance periods) should not exceed 16 weeks.

Participants who discontinue the IP should undergo a 2-week taper period. The taper period may be shortened at the discretion of the investigator as clinically indicated. Participants who discontinue the IP before the scheduled completion of the study will return to the site 2 weeks after the end of taper to complete the safety follow-up assessments.

Following completion of the double-blind phase, participants who are compliant with study conduct will have the option to enroll and be treated with GNX in a separate OLE study, 1042-TSC-3002. All participants entering the OLE will have their dose of study medication adjusted in a double-blind cross-titration over 4 weeks such that all are receiving GNX at study completion. Participants who do not continue in the OLE will undergo a 2- to 4-weeks double-blind down-titration and taper if discontinuing IP.

Study Duration for Participation

Eligible participants will collect 4 weeks of prospective baseline seizure data prior to starting treatment. Participants will be randomized (1:1) to double-blind treatment with GNX or placebo. GNX is to be titrated to target dose over 4 weeks. The total double-blind phase (titration and maintenance period) should not exceed 16 weeks.

Following completion of the treatment period, participants who are compliant with study conduct will have the option to enroll and be treated with GNX in a separate OLE study, 1042-TSC-3002.

Number of Participants

Approximately 200 participants with TSC will be screened with the aim of randomizing approximately 162 participants (81 per arm), aged 1 to 65 years (inclusive). Participants will be randomized (1:1) to either GNX or placebo as adjunctive therapy with their standard AEDs.

Number of Sites

This global, multicenter study will be conducted at approximately 60 sites (US and ex-US).

Scientific Rationale for Study Design

Children and adults with TSC-related epilepsy will be included in the study. The eligibility criteria allow for the selection of participants comparable to the patients seen in clinical practice. Randomization will be used in this study to avoid bias in the assignment of participants to treatment, to prevent introducing bias into the study evaluations and statistical analyses, and to ensure participant characteristics are balanced between the GNX and placebo arms.

All the efficacy and safety assessments included in this study are standard measures used in clinical studies in general and epilepsy trials in particular.

Justification for Dose

A minimum GNX dose of 33 mg/kg/day or 900 mg/day is generally required for assessment of efficacy during the study. Clinical studies have demonstrated that GNX has anticonvulsant activity with an acceptable safety and tolerability profile in the dose range of 900 to 1800 mg in adults and children.

Dosing will be based on doses that have been shown to be safe in children and adults in multiple studies with healthy volunteers and individuals with epilepsy. GNX is to be given as an oral suspension (50 mg/mL) with food, eg, shortly after a meal or snack.

This study plans to enroll participants as young as 1 year of age. Based on the known clearance pathway of GNX (which is primarily CYP3A4/5) and CYP3A4 maturation by the age of 1 month, the dosing strategy for pediatric participants 1 to 2 years was guided by a recently completed population PK analysis which incorporated allometric principles. The similarity of model C. and the AUC with the proposed dosing regimen across a range of doses administered in previous clinical trials in participants 2 years of age and older coupled with the known maturation of CYP3A4 indicates that a similar exposure will be achieved in participants 1 to 2 years of age with the proposed dosing regimen.

GNX (or matching volumes of placebo suspension) will be titrated at approximately weekly intervals over 4 weeks to a maximum dose based on the participant's starting weight of 63 mg/kg/day with a maximum daily dose of 1800 mg (for patients>28 kg).

In the phase 2 data for GNX in TSC there was observation of a possible interaction with CBD. In the trial of 23 treated patients, approximately half were on cannabidiol, and there was an association between higher CBD doses and increased somnolence. Given the small sample size, more definitive conclusions were not possible. As a result, participants receiving concomitant CBD (Epidiolex) must be monitored closely throughout this phase 3 protocol for adverse events (particularly those that are somnolence-related).

The maximum dose for all participants is 1800 mg/day. The total double-blind phase (titration and maintenance periods) should not exceed 16 weeks.

Dosing will be as follows:

GNX (or matching volumes of placebo suspension) will be administered TID with food, eg, shortly after a meal or snack, and titrated at approximately weekly intervals over 4 weeks based on the participant's starting weight. The titration will start on Day 1 and end on Day 28 (see Table 3), with maintenance beginning on Day 29 at the start of Week 5. An alternative titration can be considered for patients receiving greater than 10 mg/kg/day CBD (Epidiolex) (See Table 4). See, also, FIGS. 8 and 9.

TABLE 3

28 kg (62 pounds) or less

| Day | Per dose (mg/kg) | Per day (mg/kg) | % target (63 mg/kg/day) |
|---|---|---|---|
| 1 | 2 | 6 | 10 |
| 7 | 4 | 12 | 19 |
| 14 | 8 | 24 | 38 |
| 21 | 14 | 42 | 67 |
| 28 | 21 | 63 | 100 |

Greater than 28 kg (62 pounds)

| Day | Per dose (mg) | Per day (mg) | % target (1800 mg/day) |
|---|---|---|---|
| 1 | 50 | 150 | 8 |
| 7 | 100 | 300 | 17 |
| 14 | 200 | 600 | 33 |
| 21 | 400 | 1200 | 67 |
| 28 | 600 | 1800 | 100 |

TABLE 4

28 kg (62 pounds) or less

| Day | Per dose (mg/kg) | Per day (mg/kg) | % target (42 mg/kg/day) |
|---|---|---|---|
| 1 | 1 | 3 | 7 |
| 7 | 2 | 6 | 14 |
| 14 | 4 | 12 | 29 |
| 21 | 8 | 24 | 57 |
| 28 | 14 | 42 | 100 |

Greater than 28 kg (62 pounds)

| Day | Per dose (mg) | Per day (mg) | % target (1200 mg/day) |
|---|---|---|---|
| 1 | 30 | 90 | 8 |
| 7 | 60 | 180 | 15 |
| 14 | 120 | 360 | 30 |
| 21 | 240 | 720 | 60 |
| 28 | 400 | 1200 | 100 |

Dose Modification

The protocol allows some alterations from the currently outlined dosing schedule. GNX (or matching volumes of placebo suspension) will be titrated at approximately weekly intervals over 4 weeks to a maximum dose based on the participant's starting weight as described above.

Any participant may have the dose of IP temporarily or permanently decreased at any point in the maintenance period to manage tolerability. Dose adjustments to manage AEs, including alternative dosing paradigms, should be discussed with the sponsor medical monitor prior to making the change. If it is not possible to contact the medical monitor prior to the dose adjustment, the medical monitor should be notified as soon as possible after making the change.

The maximum dose for all participants is 1800 mg/day. The total double-blind phase (titration and maintenance periods) should not exceed 16 weeks. Participants who discontinue the IP should undergo a 2-week taper period. The taper period may be shortened at the discretion of the investigator as clinically indicated.

Example 3. Analysis of Adverse Events and Correlation with Efficacy in the Marigold Study of Ganaxolone in CDLK Deficiency Disorder (CDD)

The Marigold Study was a phase 3 clinical trial of ganaxolone for the treatment of CDD. The trial met primary endpoint—median 28-day major motor seizure frequency reduction of 32.2 percent compared to 4.9 percent for placebo. Ganaxolone was generally well tolerated and the discontinuation rate in the active treatment arm was less than 5 percent. The most frequent adverse event was somnolence.

Data on efficacy, as assessed by % change in atonic seizures, % change in tonic seizures, % change in clonic seizures, % change focal to bilateral tonic-clonic sz, % change generalized tonic-clonic sz, % change all focal sz and % change all major motor seizures in the ganaxolone treatment group (N=49) was analyzed for patients who experienced somnolence-related adverse event and patient who did not experience that type of adverse event. The analysis revealed in the Marigold study there was reduced efficacy in patients who experienced somnolence-related adverse events. (See, FIG. 10.) These effects are unlikely secondary to age or weight, which were balanced between the two groups. This supports the findings in the TSC study described in Example 1, in which there was also reduced efficacy in patients who experiences somnolence-related adverse events. These results indicate that the methods of this disclosure can provide effective treatment with reduced adverse events in patients with CDD.

The invention claimed is:

1. A method for treating a seizure or epilepsy disorder, comprising orally administering to a subject in need thereof ganaxolone in an amount of:
   about 150 mg per day for about one week, followed by about 300 mg per day for about one week, followed by about 600 mg per day for about one week, followed by about 1,200 mg per day for about one week, followed by about up to 1,800 mg per day for the remaining treatment period.

2. The method of claim 1, wherein the subject is concomitantly being administered cannabidiol.

3. The method of claim 1, wherein about 50 mg are administered three times a day for about one week, followed by about 100 mg administered three times a day for about one week, followed by about 200 mg administered three times a day for about one week, followed by about 400 mg administered three times a day for about one week, followed by 600 mg administered three times a day for the remaining treatment period.

4. The method of claim 1, wherein ganaxolone is administered as an oral suspension or oral solution.

5. The method of claim 1, wherein ganaxolone is administered as an oral capsule or tablet.

6. The method of claim 1, wherein the treatment period is for at least about 5 weeks or longer.

7. The method of claim 1, wherein administration of ganaxolone does not result in somnolence in the subject.

8. The method of claim 1, wherein the epilepsy disorder is a focal seizure, a generalized seizure, progressive myoclonic epilepsy, reflex epilepsy, Landau-Kleffner Syndrome, Ohtahara syndrome, Rasmussen's syndrome, infantile spasms (or West syndrome), Lennox-Gastaut syndrome (LGS), Rett syndrome, Dravet syndrome, Doose syndrome, CDKL5 deficiency disorder, tuberous sclerosis complex, intractable childhood epilepsy (ICE), childhood absence epilepsy (CAE), juvenile myoclonic epilepsy (JME), essential tremor, acute repetitive seizures, benign rolandic epilepsy, status epilepticus, refractory status epilepticus, super-refractory status epilepticus, PCDH19 pediatric epilepsy, Angelman syndrome, Doose Syndrome, Aicardi syndrome increased seizure activity, a breakthrough seizures or an infantile spasms.

9. The method of claim 1, wherein administering ganaxolone reduces the frequency of seizure in the subject relative to baseline.

10. The method of claim 1, wherein administering ganaxolone results in a reduction in seizure frequency of about 20% or greater relative to baseline seizure frequency.

11. A method for treating a seizure or an epilepsy disorder, comprising orally administering to a subject in need thereof ganaxolone in an amount of:
    about 6 mg/kg/day for about one week, followed by about 12 mg/kg/day for about one week, followed by about 24 mg/kg/day for about one week, followed by about 42 mg/kg/day for about one week, followed by up to 63 mg/kg/day for the remaining treatment period.

12. The method of claim 11, wherein about 2 mg/kg are administered three times a day for about one week, followed by about 4 mg/kg administered three times a day for about one week, followed by about 8 mg/kg administered three times a day for about one week, followed by about 14 mg/kg administered three times a day for about one week, followed by 21 mg/kg administered three times a day for the remaining treatment period.

13. The method of claim 11, wherein ganaxolone is administered as an oral suspension or oral solution.

14. The method of claim 11, wherein ganaxolone is administered as an oral capsule or tablet.

15. The method of claim 11, wherein the treatment period is for at least about 5 weeks or longer.

16. The method of claim 11, wherein administration of ganaxolone does not result in somnolence in the subject.

17. The method of claim 11, wherein the epilepsy disorder is a focal seizure, a generalized seizure, progressive myoclonic epilepsy, reflex epilepsy, Landau-Kleffner Syndrome, Ohtahara syndrome, Rasmussen's syndrome, infantile spasms (or West syndrome), Lennox-Gastaut syndrome (LGS), Rett syndrome, Dravet syndrome, Doose syndrome, CDKL5 deficiency disorder, tuberous sclerosis complex, intractable childhood epilepsy (ICE), childhood absence epilepsy (CAE), juvenile myoclonic epilepsy (JME), essential tremor, acute repetitive seizures, benign rolandic epilepsy, status epilepticus, refractory status epilepticus, super-refractory status epilepticus, PCDH19 pediatric epilepsy, Angelman syndrome, Doose Syndrome, Aicardi syndrome increased seizure activity, a breakthrough seizures or an infantile spasms.

18. The method of claim 11, wherein administering ganaxolone reduces the frequency of seizure in the subject relative to baseline.

19. The method of claim 11, wherein administering ganaxolone results in a reduction in seizure frequency of about 20% or greater relative to baseline seizure frequency.

20. The method of claim 1, wherein the subject weighs more than 28 Kg.

21. The method of claim 3, wherein the subject weighs more than 28 Kg.

22. The method of claim 11, wherein the subject weighs 28 Kg or less.

23. The method of claim 12, wherein the subject weighs 28 Kg or less.

24. The method of claim 11, wherein the subject is concomitantly being administered cannabidiol.

* * * * *